(12) United States Patent
Arizti

(10) Patent No.: US 11,354,725 B2
(45) Date of Patent: Jun. 7, 2022

(54) ABSORBENT ARTICLE SENSOR REPLACEMENT SYSTEM

(71) Applicant: The Procter & Gamble Company, Cincinnati, OH (US)

(72) Inventor: Blanca Arizti, Brooklyn, NY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 16/904,949

(22) Filed: Jun. 18, 2020

(65) Prior Publication Data

US 2021/0398195 A1 Dec. 23, 2021

(51) Int. Cl.

| G06Q 30/06 | (2012.01) |
| G06F 11/30 | (2006.01) |
| G06Q 10/00 | (2012.01) |
| G06Q 20/42 | (2012.01) |
| G01R 31/371 | (2019.01) |
| G01R 31/392 | (2019.01) |
| G06Q 20/40 | (2012.01) |
| A61F 13/42 | (2006.01) |
| G06Q 10/08 | (2012.01) |
| G06Q 30/02 | (2012.01) |
| G06F 1/28 | (2006.01) |
| G01R 31/382 | (2019.01) |

(52) U.S. Cl.
CPC ....... G06Q 30/0633 (2013.01); G01R 31/371 (2019.01); G01R 31/382 (2019.01); G01R 31/392 (2019.01); G06F 1/28 (2013.01); G06F 11/3003 (2013.01); G06F 11/3058 (2013.01); G06F 11/3065 (2013.01); G06Q 10/0837 (2013.01); G06Q 10/20 (2013.01); G06Q 20/40 (2013.01); G06Q 20/42 (2013.01); G06Q 30/0226 (2013.01); A61F 13/42 (2013.01); A61F 2013/424 (2013.01); G06Q 10/30 (2013.01)

(58) Field of Classification Search
None
See application file for complete search history.

(56) References Cited

U.S. PATENT DOCUMENTS 8,940,959 B2    1/2015  Liu
9,726,763 B2 *  8/2017  Dempsey ............ G01R 31/371
(Continued)

FOREIGN PATENT DOCUMENTS

| EP | 3184039 A1 | 6/2017 |
| EP | 3332698 A1 | 6/2018 |
| WO | 2018229017 A1 | 12/2018 |

OTHER PUBLICATIONS

All Office Actions, U.S. Appl. No. 17/346,313.
(Continued)

Primary Examiner — Roy Y Yi
(74) Attorney, Agent, or Firm — Sarah M. DeCristofaro

(57) ABSTRACT

A system includes a processor that executes computer executable components. The computer executable components include a battery monitoring component that monitors a power level of a power unit of a sensor device that removably attaches to an absorbent article configured to absorb and contain bodily exudates; and a notification component that generates a replacement notification based on a determination that the power level is below a threshold power level.

17 Claims, 12 Drawing Sheets

(56) References Cited

U.S. PATENT DOCUMENTS

| | | |
|---|---|---|
| 9,907,707 B2 | 3/2018 | Lavon |
| 9,913,608 B2 | 3/2018 | Lewis et al. |
| 10,159,607 B2 | 12/2018 | Monson et al. |
| 10,271,998 B2 | 4/2019 | Lavon |
| 10,285,871 B2 | 5/2019 | Arizti |
| 10,292,112 B2 | 5/2019 | Lavon |
| 10,624,795 B2 | 4/2020 | Christiansen et al. |
| 2005/0124947 A1 | 6/2005 | Fernfors |
| 2006/0238360 A1 | 10/2006 | Ho |
| 2008/0278336 A1* | 11/2008 | Ortega .................. A61B 5/002 340/573.5 |
| 2014/0155850 A1 | 6/2014 | Shah et al. |
| 2014/0379285 A1 | 12/2014 | Dempsey et al. |
| 2017/0252226 A1 | 9/2017 | Arizti |
| 2017/0351271 A1 | 12/2017 | Hasenoehrl |
| 2017/0353323 A1 | 12/2017 | Apte |
| 2019/0167489 A1 | 6/2019 | Hellmold et al. |
| 2020/0060886 A1 | 2/2020 | Arizti et al. |
| 2020/0088701 A1 | 3/2020 | Jung et al. |

OTHER PUBLICATIONS

All Office Actions, U.S. Appl. No. 16/905,076.
All Office Actions, U.S. Appl. No. 16/904,936.
Unpublished U.S. Appl. No. 16/904,936, filed Jun. 18, 2020, to first inventor et. al.
Unpublished U.S. Appl. No. 16/905,076, filed Jun. 18, 2020, to first inventor et. al.
Unpublished U.S. Appl. No. 17/346,313, filed Jun. 14, 2021, to first inventor et. al.
15755-WO Search Report and Written Opinion for PCT/US2021/037981 dated Oct. 15, 2021, 12 pages.

* cited by examiner

ABSORBENT ARTICLE SENSOR REPLACEMENT SYSTEM

TECHNICAL FIELD

This application relates to sensor systems and more particularly to techniques for replacing battery depleted sensor devices designed to be reused with absorbent articles.

BACKGROUND

Absorbent articles for personal hygiene, such as disposable diapers for infants, training pants for toddlers or adult incontinence undergarments are designed to absorb and contain bodily exudates. These absorbent articles comprise several layers providing different functions, for example a topsheet, a backsheet and in-between an absorbent core, among other layers. The function of the absorbent core is to absorb and retain the exudates for a prolonged amount of time, minimize re-wet to keep the wearer dry and avoid soiling of clothes or bed sheets.

It has been proposed to incorporate sensors into absorbent articles to facilitate sensing information about the usage of the article and/or the activity of the wearer (e.g., timing of initiation and level of saturation associated with urination and/or defecation) and/or providing notifications to users (e.g., caregivers, article manufacturers, etc.) regarding said information. It is preferable to integrate a non-rechargeable battery into these sensors to prevent time lags in use when the device is being charged. Consequently, manufacturers desire mechanisms to ensure customers are provided with replacement sensor devices or replacement batteries prior to complete battery depletion. Further, it is desirable that consumers receive proper replacements (e.g., replacement power sources that carry a charge for the same amount of time as the initial power source, that are compatible with the sensor device, that are not counterfeit, etc.).

Therefore, there is a need for mechanisms that detect nearly depleted power sources and initiate replacement sensors/power sources based on said detection. There is also a need for mechanisms that ensure suitable replacements or refurbishments are provided for used, broken or lost sensor devices/power sources. There is also a need for mechanisms to ensure and track authorized use and/or replacement of products by manufacturers or their designees to, for example, provide loyal customers with rewards and/or ancillary services.

SUMMARY

A system is provided that comprises a processor that executes the computer executable components. These computer executable components include a battery monitoring component that monitors a power level of a power unit of a sensor device that removably attaches to an absorbent article configured to absorb and contain bodily exudates. The computer executable components further comprise a notification component that generates a replacement notification based on a determination the power level is below a threshold power level. In one or more embodiments, the battery comprises a non-rechargeable battery.

A method is provided that comprises monitoring, by a system comprising or operative coupled to a processor, power unit replacement information of a sensor device. The sensor device removably attaches to an absorbent article configured to absorb and contain bodily exudates. The method further comprises generating, by the system, a replacement notification based on a determination the sensor device is performing below a threshold performance level, a power level is below a threshold power level, a power unit of the sensor device has met a threshold time in use and/or age, and combinations thereof.

A system is provided that comprises a processor that executes the computer executable component. The computer executable components can include a request receipt component that receives a request to replace or refurbish a sensor device that attaches to an absorbent article configured to absorb and contain bodily exudates. The request comprises comprising attribute information indicating one or more attributes of the sensor device. The computer executable components further comprise an order processing component that selects a replacement sensor device for the sensor device based on the attribute information and facilitates a shipment of the replacement sensor device to an address associated with the request.

Elements described in the disclosed systems can be embodied in different forms such as a computer-implemented method, a computer program product, or another form.

DETAILED DESCRIPTION

Figure 1:
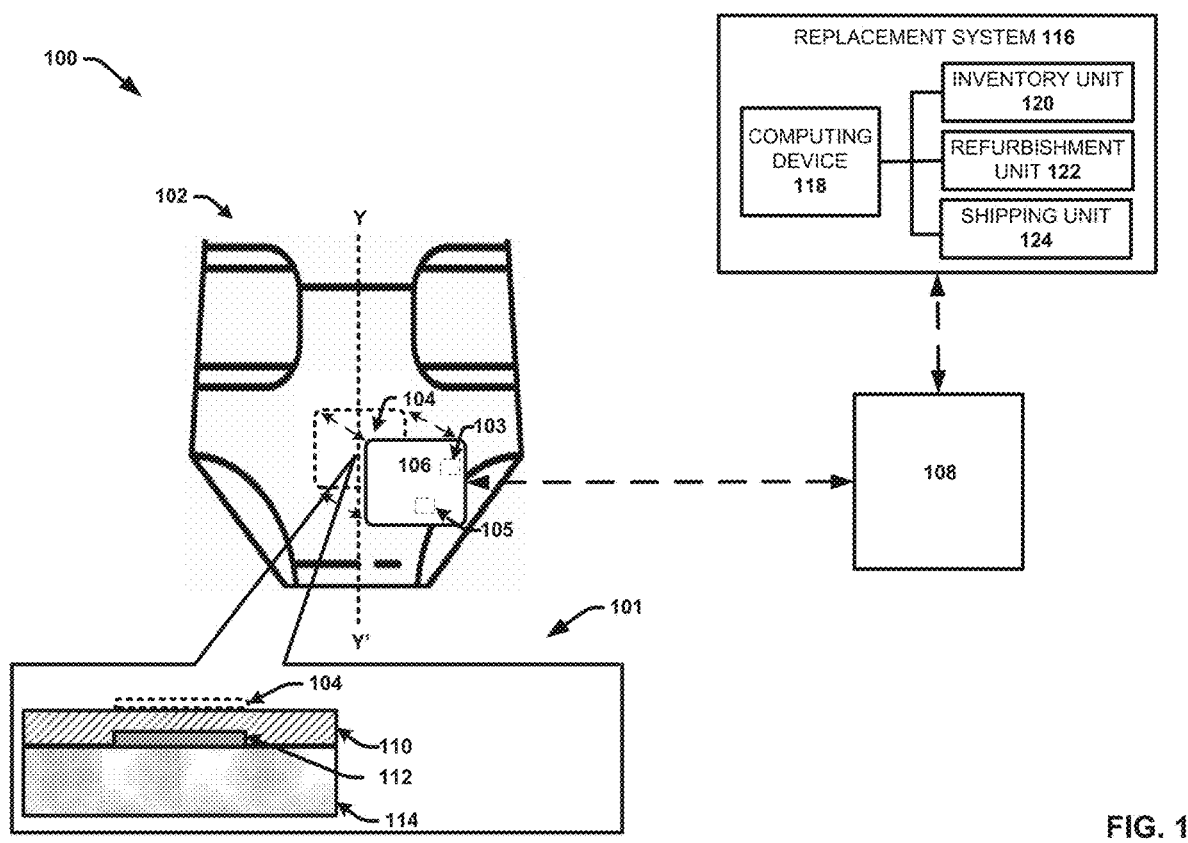
FIG. 1 illustrates a block diagram of an example, non-limiting system that facilitates replacing battery depleted sensor devices designed to be reused with absorbent articles in accordance with one or more embodiments of the disclosed subject matter.

The following detailed description is merely illustrative and is not intended to limit embodiments and/or application or uses of embodiments.

The disclosed subject matter is directed to a sensor device replacement system that facilitates replacing or refurbishing sensor devices that attach to absorbent articles. The sensor device replacement system facilitates ensuring used (e.g., battery depleted) and/or damaged sensor devices are replaced with new and/or refurbished sensor devices from an authorized manufacturer (e.g., prior to complete battery depletion) and mitigates unauthorized refurbishment/replacement of used or damaged sensor devices.

In one or more embodiments, the sensor device and/or an external device communicatively coupled to (i.e. paired with) the sensor device can monitor certain information indicative of the need for replacement of the power unit of the sensor device and generate a notification. The system can comprise one or more computer executable components to facilitate sending the notification as well as facilitate ordering a replacement, authorizing a replacement order, shipping a replacement, issuing rewards, providing return information, and combinations thereof. Further to the above, the sensor device can also employ an outer cover formed around the power unit that cannot be removed without damaging the outer cover. These and other features will be discussed in more detail below.

"Absorbent article" as used herein refers to a variety of devices which are placed or worn against or in proximity to the body of the wearer to absorb and contain various exudates discharged from the body, such as disposable diapers. Typically, these absorbent articles comprise a topsheet, a backsheet, an absorbent core and optionally an acquisition system (which may be comprised of one or several layers) and other components, with the absorbent core normally placed between the backsheet and the acquisition system or topsheet. The function of the absorbent core is to absorb and retain the exudates. Although various embodiments of the disclosed subject matter are exemplified in association with the absorbent article being a disposable diaper, it should be appreciated that the disclosed techniques can be applied to a variety of other types of absorbent articles, including reusable diapers (e.g., cloth diapers), absorbent inserts which may be disposable or reusable and may be used in combination with reusable outer covers, pants, training pants, pads, adult incontinence products, and/or feminine hygiene products (including, for example, sanitary napkins and tampons).

"Sensor device" refers to any electrical device that can be attached to and/or integrated on or within an absorbent article that provides for capturing and/or generating sensory feedback data associated with wear of the absorbent article via one or more sensors formed on or within the sensor device. In various embodiments, the sensor device can be configured to removably attach to disposable diapers and/or other absorbent articles.

"Sensory feedback data" (or simply "sensory feedback") as used herein refers to any type of data captured by one or more sensors formed on or within the sensor device and/or determined or inferred based on the captured sensor data. In this regard, unless context warrants particular distinctions among the terms, sensory feedback data can include raw sensor measurements (e.g., raw color sensor data, raw motion sensor measurements, etc.) and/or processed feedback information determined based on the raw sensor measurements using one or more algorithms, heuristics, machine learning models, etc. (e.g., a determined saturation/wetness level, a determined activity level, etc.). Sensory feedback data includes usage data and/or activity data.

"Power unit replacement information" as used herein refers to information that can be used to determine if a power unit for a sensor device needs, or will need, replacement or refurbishment. Non-limiting examples of power unit replacement information include the power level of a power unit, the age of the power unit, the age of the sensor device, connectively of the power unit to the sensor device or to the system incorporating the sensor device, time-in-use of the power unit (i.e., how long the power unit has been providing power), performance of the power unit and/or of the sensor device (e.g., performance as measured by or in reference to predetermined metrics), time-in-use of the sensor device, amount of output from the sensor device and combinations thereof.

"Usage" in relation to information captured, to be captured, inferred/determined from information captured, processed, detected, stored and/or transmitted, or otherwise used in the sensor systems described herein refers information regarding occurrence and/or timing of the exudation events (e.g., urination, defecation), amount of bodily exudates (e.g., by volume, by weight) associated with an exudation event, saturation levels, time to saturation of the absorbent article, loading status, amount of bodily exudates contained within the absorbent article over a period of time, frequency of exudation events, frequency of article changes, duration of exposure time to bodily exudates, type of the bodily exudates (e.g., urine, feces, discharge, etc.), characteristics of the bodily exudates (e.g., runny bowel, mushy/pasty bowels, viscosity of exudates, coloration of the exudates, etc.), biomarkers present in the bodily exudates, and/or other details related to the use of an absorbent article.

"Activity" in relation to information captured, to be captured, inferred/determined from information captured, processed, detected, stored and/or transmitted, or otherwise used in the sensor systems described herein refers to information regarding exertion levels, movement, exertion and/or movement patterns, sleep/wake patterns, positions, motions, defined movements and motions (e.g., laying, laying on back, laying on stomach, sitting, kicking, walking, crawling, grabbing/pulling on diaper, etc.), and/or other details related to the actions of the wearer during wear of an absorbent article.

"Joined" or "attached" as used herein encompasses configurations whereby an element is directly secured to another element by affixing the element directly to the other element, and configurations whereby an element is indirectly secured to another element by affixing the element to intermediate member(s) which in turn are affixed to the other element. The terms further include embodiments in which a pocket or other connector is formed in or attached to an area of the absorbent article. Further, these terms include configurations in which the elements are removably or non-removably attached.

"Processor" as used herein refers to a device that executes machine/computer executable instructions or components stored in memory. A processor as used herein includes, but is not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize use of space or enhance performance of user equipment. A processor can also be implemented as a combination of computing processing units.

"Component" as it relates to a sensor device, a system incorporating a sensor device and/or other machinery herein refers to a computer-related entity or an entity related to an operational machine with one or more specific functionalities. The entities may be hardware, software, a combination of hardware and software, or software in execution. One or more components can reside within a process and/or thread of execution and a component can be localized on one computer and/or distributed between two or more computers. Components can communicate via local and/or remote processes. A component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system. Embodiments of systems described herein can include one or more machine-executable components embodied within one or more machines (e.g., embodied in one or more computer-readable storage media associated with one or more machines). Such components, when executed by one or more machines (e.g., processors, computers, computing devices, virtual machines, etc.) can cause the machine(s) to perform the operations described.

"Memory" as used herein refers to mechanism(s) used to retain information, such as executable instructions or components. As used herein, terms such as "store," "storage," "data store," data storage," "database," and substantially any other information storage element relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

One or more embodiments are now described with reference to the drawings. In the following description, numerous specific details are set forth in order to provide a more thorough understanding of the embodiments. It is evident, however, that the embodiments can be practiced without these specific details. In addition, certain elements may be left out of particular views for the sake of clarity and/or simplicity when explanations are not necessarily focused on the omitted elements.

FIG. 1 illustrates a block diagram of an example, non-limiting system 100 that facilitates replacing sensor devices designed to be reused with absorbent articles. Embodiments of systems described herein can include one or more machine-executable components embodied within one or more machines (e.g., embodied in one or more computer-readable storage media associated with one or more machines). Such components, when executed by the machine(s) (e.g., processors, computers, computing devices, virtual machines, etc.) can cause the machine(s) to perform the operations described.

System 100 includes an absorbent article 102, a sensor device 106 having a power unit 105, an external user device 108 and a replacement system 116. In the embodiment shown, the absorbent article 102 is a diaper, such as a disposable diaper. However, it should be appreciated that the absorbent article 102 can be or include a variety of other types of absorbent articles.

Components of the absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels, leg gasketing systems, superabsorbent, acquisition layers, core wrap materials, adhesives, outer covers, fastener systems, and landing zones. In at least one embodiment, an absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the absorbent article component can be ground into particulates less than about 20 mesh using known grinding methods (e.g., WILEY® mill), and a representative sample of suitable mass taken from the randomly mixed particles.

In one or more embodiments, the sensor device 106 is configured to removably attach to the absorbent article 102 and capture sensory feedback associated with wear of the absorbent article 102 using one or more sensors 103 formed on or within a housing (described infra) of the sensor device 106. Although system 100 depicts a single absorbent article for use with the sensor device 106, the sensor device 106 can be designed to be reused with and reattached to a plurality of absorbent articles. The sensor device 106 can be configured to removably attach at or near an attachment zone 104 disposed on exterior portion of the absorbent article 102. The location of the attachment zone 104 can vary depending on the type of the absorbent article 102, the type of sensory data the sensor device 106 is configured to capture/detect, and/or the mechanism via which the sensor device 106 captures/detects the sensor data in association with attachment to the absorbent article 102.

The sensor device 106 can be configured to capture and/or generate sensory feedback data regarding usage and/or activity. In various implementations, the sensor device 106 can capture and/or detect information based on responses/reactions reflected in one or more indicators 112. With these implementations, the absorbent article 102 can comprise one or more indicators 112 formed on or within the absorbent article 102 that generate a response/reaction to indicate certain information (e.g., the presence and/or absence of bodily exudates), and the sensor device 106 can include one or more sensors configured to detect the response/reaction.

For example, call out box 101 presents an enlarged view of a transversal cross-section of a portion of the absorbent article 102 taken along axis Y-Y' in accordance with some example embodiments. As shown in call out box 101, in some embodiments, the absorbent article 102 can comprise a backsheet 110 is an outer layer of the absorbent article 102. The absorbent article 102 can further include one or more internal layers 114 formed on or joined to the backsheet 110. Such internal layers 114 may include one or more layers of an acquisition system, one or more layers of an absorbent core, and/or one or more layers of the backsheet. The absorbent article 102 can further include one or more indicators 112 formed between the backsheet 110 and at least one of the internal layers 114 within a region of the absorbent article that at least partially overlaps the attachment zone 104 to which the sensor device 106 is intended to be attached. For example, in some embodiments, the housing (discussed infra with reference to FIGS. 2A and 2B) of the sensor device 106 can be adapted to be physically coupled to the absorbent article 102 such that the sensor device 106 is further communicatively coupled to one or more indicators 112.

In some embodiments, at least one indicator 112 may react to usage and/or activity information (or other conditions to be monitored) via one or more changes in a property of the indicator (e.g., a physical, chemical and/or biological property such as color, smell, sound, pH, or the like). By way of nonlimiting example, the indicator 112 may react to the presence and/or absence of bodily exudates and/or one or more properties of those bodily exudates. The property or state of the indicator 112, in turn, can be detected by one or more sensors when the sensor device 106 is physically and/or communicatively coupled to the absorbent article 102. In one particular implementation, the indicator 112 can comprise an optical property changing composition or device (e.g., a color-changing composition or device, such as a color changing indicator) that changes an optical property based on the presence and/or absence of bodily exudates within the internal layers 114. A color changing indicator can change its color, for example, based on the presence and/or absence of bodily exudates and/or in response to some other condition being monitored.

Essentially any known color-changing indicator that responds to the absence or presence of bodily exudates or other conditions to be monitored with respect to the absorbent article 102 can be used. In some implementations, the absorbent article 102 can employ a color-changing indicator, such as a color strip, which comprises a chemical substance that can induce a color change in the color strip when bodily exudates are present within the internal layers 114. One useful form of a color-changing indicator comprises a pH-sensitive indicator. With these implementations, the sensor device 106 can include one or more optical sensors, such as a color sensor (also referred to as a colorimeter), to detect information based on detection of a defined color change in the color indicator. For example, the color sensor can provide an output that varies depending on usage information (e.g., the presence or absence of bodily exudates, an amount of the bodily exudates), which is identified/detected by an optical property (e.g., a color) in the color indicator that is observed by the sensor.

The indicator 112 is not limited to pH sensitive color strip indicators but rather can include any indicator that changes color, or another physical property, directly or indirectly related to usage of the article and/or wearer activity. For example, color change materials that change from no color to one or more colors, from one or more colors to no colors, change colors in other color ranges than the pH sensitive adhesive described herein, materials that change color or appearance based on factors other than pH changes, such as but not limited to, temperature, wetness, odor, enzymes, organic components, inorganic components (e.g., salt level), colored SAP/AGM, mechanical forces (e.g., strain, stretch) or the like.

Indicators 112 can also comprise biological or physical sensor materials. For example, physical sensors can be provided by a material, which changes its color when the material is stretched. Stretching of a material can be induced by the swelling of the absorbent core, or other portions, of the absorbent article 102. Biological sensors can include a bioreceptor that interacts with an analyte of interest, such as trypsin or urease. A bioreceptor, for example, can use reagent/analyte interactions that provide a property change (e.g., a color or other optical change) in the absorbent article 102 upon detection of a particular analyte of interest (e.g., a biomarker). Additionally, or alternatively, a bioreceptor can use an immobilized binding reagent capable of binding to an analyte of interest. The immobilized reagent can be disposed on or within one or more layers of the absorbent article 102 adjacent to the attachment zone 104.

Additionally, or alternatively, the indicators 112 can comprise a material selected from the group comprising, consisting essentially of or consisting of: thermochromic inks, thermochromic dyes, thermochromic liquid crystalline materials, and combinations thereof. These indicators can, for example, serve to monitor other conditions associated with the absorbent article and/or wearer of the absorbent article, such as body temperature or fever indication.

The sensor device 106 can include various other types of sensors 103 that can capture and/or generate sensory feedback data regarding usage of the absorbent article and/or activity of the wearer. The sensor device 106 can include one or more motion sensors (e.g., an accelerometer, a gyroscope, etc.), image sensors, biosensors, biochemical sensors, temperature sensors, force/pressure sensors, humidity sensors, acoustic sensors, an RFID reader/sensor, biofeedback sensors configured to detect physiological parameters associated with the wearer (e.g., heart rate, temperature, and other vital signs, biomarkers present in bodily exudates and the like), and the like. Additionally, or alternatively, at least one sensor can be configured to sense, detect or otherwise capture sensor data reflective on a behavior of the wearer, pressure and irritation associated with fit and/or wear of the absorbent article, and the like. Further, the activity information can include motion and/or movement data (e.g., captured via one or more motion sensors) that can be correlated to defined bodily movements and/or positions, movement patterns, activity patterns (e.g., sleep/wake patterns), activity levels, and the like.

In addition to one or more sensors, the sensor device 106 can further include suitable electronic circuitry (e.g., hardware), software, or a combination thereof, that provides for processing of raw sensor measurements representative of a measured property (e.g., a wetness/saturation level, an amount of bodily exudates, an activity level, an activity pattern, a defined movement or motion, etc.) as captured via the sensor(s) of the sensor device 106 into a digital signal corresponding to the measured property. For example, such electronic circuitry can include but is not limited to, excitation control elements, amplification elements, analogue filtering elements, data conversion elements, compensation elements, and the like. As described in greater detail infra with reference to FIG. 5, the sensor device 106 can also include or be operatively coupled to at least one memory that stores computer executable instructions and at least one processor (e.g., a microprocessor) that executes the computer executable instructions stored in the memory.

The sensor device 106 can also include suitable communication hardware and/or software that provides for wireless and/or wired communication between the sensor device 106 and at least one external user device 108. The external user device 108 can include essentially any type of computing device capable of at least receiving information from the sensor device 106. For example, the external user device 108 can include but is not limited to: a mobile phone, a smartphone, a smartwatch, a tablet personal computer, a laptop computer, a desktop computer, a video monitoring device (e.g., a video baby monitor device), an audio monitoring device (e.g., an audio baby monitor device), an augmented reality (AR) device, a virtual reality (VR), a heads-up display (HUD), a smart speaker device, another sensor device, an IoT device, a television, an Internet enabled television, and similar types of devices.

For example, in some embodiments, the sensor device 106 can be configured to transmit captured sensor data to an external user device 108 associated with a caregiver and/or the wearer (or another suitable entity) for processing and/or presentation to the caregiver etc. via a display, speaker, or another suitable output device of the external user device 108. The external user device 108 can be configured to process and/or analyze the sensor data to determine and/or infer sensory feedback data based on captured sensor measurements. For example, the external user device 108 can receive sensor data from the sensor device 106 identifying or indicating a measured property and/or status of at least one indicator 112. In another example, the external user device 108 can receive sensor data including chemical sensor measurements, temperature sensor measurements, motion sensor measurements, pressure sensor measurements, and the like, as captured via corresponding sensors located on or within the sensor device 106. The external user device 108 can further process/analyze the received sensor data using predefined processing logic (e.g., algorithms, heuristics, machine learning models, defined correlations, tracked data correlations, etc.) to determine or infer sensory feedback data. In some embodiments, the external user device 108 can further present or otherwise render the sensory feedback information at the external user device 108. For example, based on a determination that the sensor data indicates the diaper is wet, the external user device 108 can generate and render a notification at the external user device notifying the caregiver that the article needs changing. In addition to processing and/or rendering the captured sensor data to provide feedback to the user, the sensor device 106 and/or the external user device 108 can also store the sensor data and/or the feedback data determined therefrom in suitable data storage for data aggregation.

The sensor device 106 itself can include onboard processing logic for processing some or all of the sensor data to determine or infer sensory feedback data based on the captured sensor data measurements. With these embodiments, the sensor device 106 can be configured to transmit the processed sensory feedback data to the external user device 108 for presentation to the device user and/or for further analytical processing (e.g., by the external user device 108, an application server for the connected care system, another system or the like). For example, the sensor device 106 can include onboard processing logic that can determine when the absorbent article 102 has reached a threshold saturation level and thus requires changing based on a color property or other measured property of color changing wetness indicator provided on or within the absorbent article. Based on a determination that the threshold saturation level has been reached, the sensor device 106 can be configured to transmit a notification to the external user device 108 that indicates the absorbent article 102 has reached the threshold saturation level. The external user device 108 can further render the notification using an appropriate rendering mechanism (e.g., as a visual notification rendered via a display, as an audible alarm, or the like).

The external user device 108 and/or the sensor device 106 can further be communicatively coupled to one or more additional devices and/or systems via a suitable communication network (e.g., the Internet). For example, in the embodiment shown, the external user device 108 is communicatively coupled to a replacement system 116 that includes at least one computing device 118 (e.g., which can include a real or virtual machine computing device). As described in greater detail infra with reference to FIG. 6, the replacement system 116 can facilitate providing customers with replacement sensor devices and/or replacement power units based in part on receipt of a replacement notification identifying a depleted, lost, or broken sensor device and/or power unit needs replacing with a new or refurbished sensor device. In various embodiments, the external user device 108 can generate and send the replacement notification to the replacement system 116 based on power unit replacement information, such as a determination that a power level of the power unit is below a threshold power level, the sensor is performing below a performance threshold (i.e., performing outside of predetermined metrics) a determination that a power level of a power unit 105, the power unit has met a predetermined time-in-use and/or age, and combinations thereof. In non-limiting examples, the power unit comprises a non-rechargeable battery 105B as shown in FIG. 2B.

Returning to FIG. 1, the sensor device 106, the external user device 108 and the replacement system 116 (e.g., the computing device 118 of the replacement system 116) can include suitable communication hardware and/or software that provides for communication between the respective devices. For example, the sensor device 106, the external user device 108, and/or the replacement system 116 can be communicatively coupled via one or more networks (e.g., a personal area network (PAN), a local area network (LAN), a wide area network (WAN) such as the Internet, and the like). The sensor device 106, the external user device 108, and/or the replacement system 116 can employ various suitable wired and/or wireless communication technologies to communicate information therebetween. For example, some suitable communication technologies/protocols can include but are not limited to: Bluetooth®, Bluetooth low energy BTLE®, Mesh (e.g., IEEE 802.15.4), WiFi (e.g., IEEE 802.15.11), communication incorporating all or any portion of IEEE 802 or similar communication standards, RFID technology, near field communication (NFC), 3G communication, 4G communication, 5G communication, Backscatter communication, light communication, audio/sound communication, harvesting protocol communication (e.g., a metadata harvesting protocol), and the like. Other communications protocols or combinations of communications protocols (e.g., a Bluetooth/Mesh combined protocol) can be employed. Additionally, or alternatively, an acoustic or optical broadcasting can be employed. Although system 100 depicts a single external user device, it should be appreciated that the sensor device 106 can be configured to communicate with a plurality of external devices of varying types (e.g., user devices, routers, monitors, other sensor devices, server devices, cloud-based systems, edge-based systems etc.).

As noted, the sensor device 106 comprises a suitable power source/unit 105 to drive the functionality of the sensor device 106 and to provide power to the various electrical components of the sensor device 106. The power unit can include but is not limited to: a battery, a capacitor, a charge pump, a mechanically derived power source (e.g., microelectromechanical systems (MEMs) device), or an induction component. In various exemplary embodiments, the power unit comprises a non-rechargeable battery 105B. By using a non-rechargeable battery as the power source, the sensor device 106 can continue to be used for a prolonged period of time (e.g., about three months) without requiring recharging. As a result, the sensor device 106 can be continuously be reused with each absorbent article change, thereby enabling continuous monitoring of usage and/or activity.

In various embodiments, the sensor device 106 and/or the external user device 108 is/are configured to monitor power unit replacement information. In non-limiting examples, the sensor device 106 and/or the external user device can be configured to monitor the power level of the power unit and determine when the power level is less than a threshold power level (e.g., 10% remaining battery power, 20% remaining battery power, 30% remaining battery power, etc.). For example, the threshold power level can be based on a minimum amount of remaining battery power needed to maintain operation of the sensor device 106 for a duration of time until the replacement system 116 can provide the user with a replacement (e.g., 24 hours, 48 hours, one week, etc.). To this end, in some embodiments, the sensor device 106 itself can monitor the power level of its power unit and send a notification to the external user device 108 when the power level is less than the threshold level. Additionally, or alternatively, the external user device 108 can ping the sensor device 106 to check its power level (e.g., once a day, or more or less frequently). Additionally, or alternatively, the sensor device 106 can include information identifying its current power level when reporting detected wetness events or otherwise reporting sensory measurements/feedback to the external user device 108. The external user device 108 can further determine when the power level of the sensor device 106 is below the threshold level based on the power level reported by the sensor device 106.

In further non-limiting examples, the sensor device 106 and/or the external user device can be configured to monitor the performance level of the power unit and/or of the sensor device and determine when the performance level is less than a threshold performance level. The threshold performance level may be provided by one or more metrics (e.g., response of sensor device to a ping from another device, amount of power generated, amount of sensory feedback output compared to user input information, temperature of the power unit and/or sensor device, time to reach certain power levels and combinations thereof). The sensor device 106 itself can monitor its performance level or the performance level of its power unit and send a notification to the external user device 108 when the performance level is less than the threshold level. Additionally, or alternatively, the external user device 108 can ping the sensor device 106 to check its performance level (e.g., once a day, or more or less frequently). Additionally, or alternatively, the sensor device 106 can include information identifying its current performance level when reporting one or more sensory measurements/feedback to the external user device 108. The external user device 108 can further determine when the performance level is below the threshold level based on the performance level reported by the sensor device 106.

Additionally, or alternatively, the sensor device 106 and/or external user device 108 can be configured to monitor the time-in-use of the power unit and/or sensor device, the age of the power unit and/or sensor device, and combinations thereof. In non-limiting examples, the system can compare the time that the power unit has been providing power with the expected runtime for such a power unit in such a device. Likewise, the system can compare the time that the sensor device has been operating to an expected runtime for such as sensor device and determine the expected remaining runtime of the power unit and/or sensor device. A time-in-use threshold may be set based on a minimum amount of power unit runtime (and/or sensor device runtime) needed to maintain operation of the sensor device 106 for a duration of time until the replacement system 116 can provide the user with a replacement (e.g., 24 hours, 48 hours, one week, etc.). Further, the system can compare the age of the sensor device and/or the age of the power unit to the expected age of similar sensor devices or power units respectively before the respective unit or device is no longer operational. A threshold age may be set a minimum remaining life needed until the replacement system 115 can provide the user with a replacement.

In some implementations, based on a determination that the power unit and/or sensor device is near, below or at a threshold and/or triggering conditions are met (i.e., other indicators of the need for replacement such as a report of a lost sensor device through an external user device), the external user device 108 and/or an application executed by the external user device 108 can be configured to automatically order a new/replacement sensor device with the replacement system 116. The replacement sensor device may comprise a new sensor device or a refurbished sensor device. Where applicable, the same sensor device can be provided with a new or refurbished power unit. The replacement sensor device 106R, as shown in FIG. 2C, may include any of the features and functionalities of the sensor device 106.

In some non-limiting examples, the application can generate a prompt for presenting (e.g., via a display at the external device) to the user at the external user device 108 notifying the user regarding power unit replacement information, more particularly power unit replacement information indicating the need for replacement. For example, the prompt can include information identifying the current power level of the sensor device 106, the remaining power level of the sensor device 106, and/or the remaining operating time of the sensor device until the battery will be depleted. The prompt can also ask the user for authorization to order a replacement sensor device with the replacement system 116. The application can further generate and send the order to the replacement system 116 for the new sensor device based on receipt of input authorizing the order.

The replacement system 116 can further facilitate completing the order and sending a replacement sensor device 106R to an address associated with the replacement order. For example, in the embodiment shown, the replacement system 116 can include an inventory unit 120, a refurbishment unit 122 and a shipping unit 124. In various embodiments, the inventory unit 120 can include or correspond to a physical stock keeping unit (e.g., a warehouse or the like) where new and/or refurbished sensor devices that correspond to sensor device 106 are stored. The refurbishment unit 122 can include or correspond to a physical environment where used, depleted or broken sensor devices and/or power units are refurbished. For example, in some implementations, the refurbishment unit 122 can receive battery depleted sensor devices and refurbish them to incorporate new and/or refurbished power units. The refurbished sensor devices can then be stored in the inventory unit 120.

In some embodiments, the refurbishment process can involve removing an outer cover of the sensor device to expose the internal electrical components (e.g., a spent battery), replacing or fixing the power unit or other electrical components as necessary, and forming a new outer cover around the electrical components. As discussed in greater detail infra with reference to FIGS. 3A and 3B, in some embodiments, the outer cover can be formed in a manner around the electrical components such that removal of the outer cover to expose the internal electrical components of the sensor device 106 requires breaking the outer cover (e.g., via cutting, splitting, cracking, etc.) or otherwise rendering the outer cover unusable with another device. The outer cover can also be formed with a proprietary mold and/or molding technique to mitigate refurbishment of the sensor devices by unauthorized third parties. The shipping unit 124 can include or correspond to a physical environment/system that handles shipping out sensor devices from the inventory unit 120 and/or receiving used, depleted or broken sensor devices for provision to the refurbishment unit 122.

To this end, the computing device 118 can serve as central operations manager and can include logic for coordinating, managing and controlling execution of operations at the respective units. For example, in some implementations, the computing device 118 can store and/or access relevant information associated with the respective units (e.g., the inventory unit 120, the refurbishment unit 122 and/or the shipping unit 124). In this regard, the computing device 118 can be communicatively coupled with one or electronic databases associated with the respective units. The computing device can also be communicatively and/or operatively coupled to one or computers and/or machines associated with the respective units and remotely control the respective computers and/or machines.

For example, the computing device 118 can access or otherwise receive inventory information associated with the inventory unit 120. The inventory information can identify available replacement sensor devices that correspond to sensor device 106. The inventor information can provide additional attributes/details associated with the replacement sensor devices, such as information identifying the make/model of the sensor devices, the type of battery employed by the respective sensor devices, the size of the battery, the physical location of the sensor devices (e.g., the warehouse/store location, the room location, the shelf location, etc.), and the like. The computing device 118 can further employ the inventory information to identify and select an appropriate replacement sensor device that corresponds to a depleted, broken or lost sensor device identified (or otherwise indicated) in a replacement order request. The computing device 118 can further interface with the shipping unit 124 to coordinate and manage delivery of the replacement sensor device to a designated address associated with the replacement order request. In various embodiments, one or more aspects of replacement process can be completed with no or little manual intervention. For example, in some embodiments, the inventory unit 120 and/or the shipping unit 124 can use robotic devices and other warehouse automation technologies to retrieve, label, and/or ship replacement sensor devices directly from their inventory/warehouse location to the end user. Such warehouse automation technologies can include but are not limited to, automated storage and retrieval systems (AS/RS), goods-to person (G2P) technology, automated guided vehicles (AGVs), automated guided carts (AGCs), autonomous mobile robots (AMRs), articulated robotic arms, autonomous delivery drones, and the like.

The replacement system 116 can also facilitate returning depleted, damaged, or otherwise used sensor devices (e.g., sensor device 106) to the replacement system 116. For example, in some embodiments, the computing device 118 can coordinate and manage the refurbishment process with the refurbishment unit 122. The computing device 118 can also manage and/or remotely control one or more aspects of the refurbishment process using automated machines and/or a combination of machine automation and manual labor. The replacement system 116 can also provide the consumer with delivery instructions, labeling and/or packaging material to facilitate returning the used sensor device. For example, the replacement system can provide the consumer with the delivery instructions, labeling (e.g., a return QR code or bar code), packaging material etc., for returning the used sensor device in association with sending the consumer a notification regarding replacement, receiving an order for replacement, and/or fulfilling a replacement order. As will be discussed below, the replacement system 116 can further provide customers with a reward (e.g., a coupon or discount issued to the user's account) for ordering replacement sensor devices with the replacement system 116 and/or for returning used sensor devices.

Figure 2A:
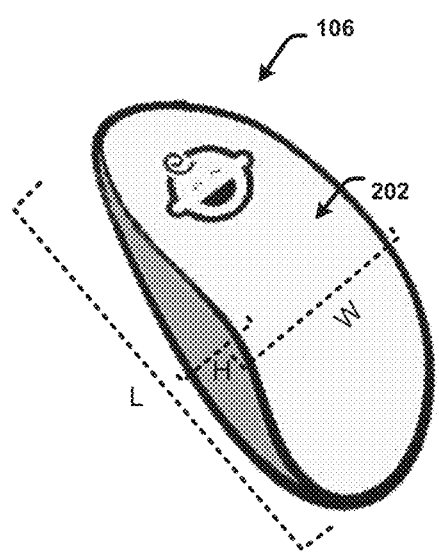
FIGS. 2A and 2B present a schematic illustration of an example sensor device in accordance with one or more embodiments of the disclosed subject matter.
Figure 2B:
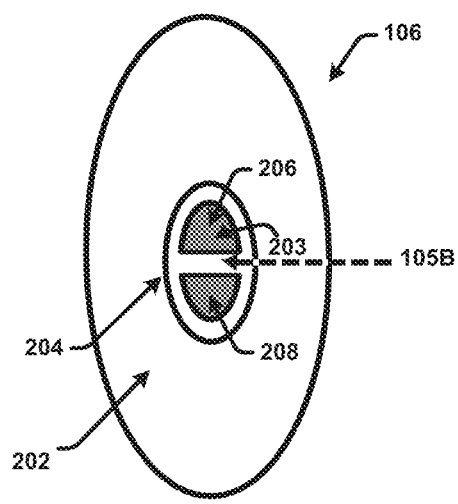
Figure 2C:
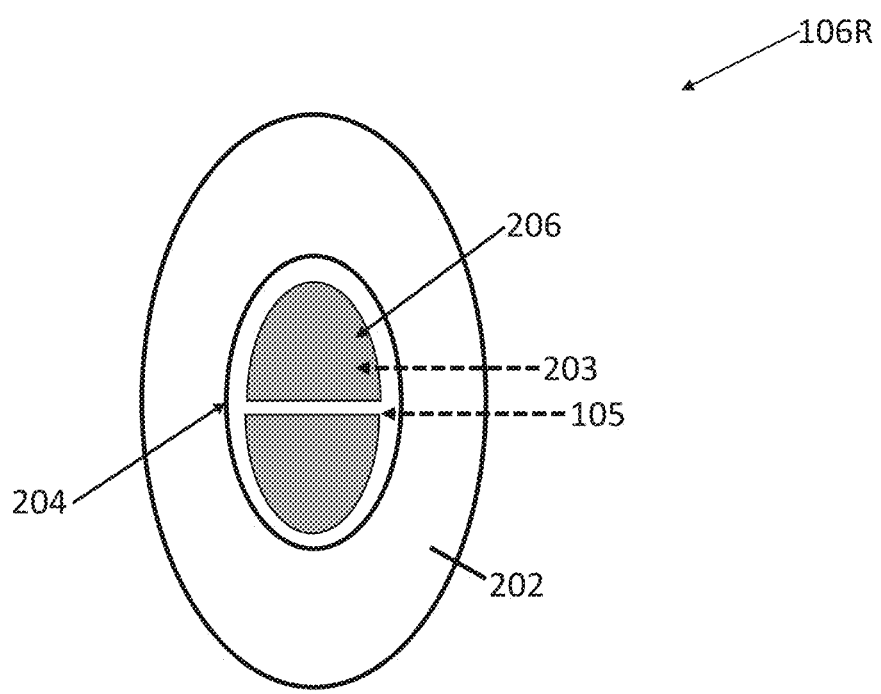
FIG. 2C illustrates a schematic illustration of an example replacement sensor device in accordance with one or more embodiments of the disclosed subject matter.

Turning to FIGS. 2A and 2B, a schematic illustration of an exemplary sensor device 106. FIG. 2A presents a three-dimensional view of top (garment-facing) and side surfaces of the housing 202. FIG. 2B presents a two-dimensional view the backside (wearer-facing side) of the sensor device 106, wherein the backside of the sensor device opposes the topside of the housing that includes the baby image/symbol as shown in FIG. 2A, and wherein the backside of the housing 202 is adapted to be attached to and face the attachment zone 104 of the absorbent article. FIG. 2C is a schematic illustration of an exemplary replacement sensor device 106R, with the backside (garment-facing side) facing the viewer. Replacement sensors can include any of the features or functionalities discussed herein with respect to sensor devices 106, 316, 416 herein and can be incorporated into any of the disclosed systems.

With reference to FIGS. 2A and 2B in view of FIG. 1, in various embodiments, the housing 202 and/or the absorbent article 102 can include one or more connectors (not shown) for removably attaching the sensor device 106 to the absorbent article 102. The connectors can be provided such that the sensor device 106 can be attached to and detached from the absorbent article 102. In non-limiting examples, the sensor device 106 can be attached and detached to an area of the absorbent article at least partially overlapping an indicator 112.

For example, in various embodiments, the housing 202 and/or the absorbent article 102 can employ various connectors which allow for detachment and can also allow for refastening of the sensor device 106 to the absorbent article 102 at or near the attachment zone 104. In some implementations, the connectors can include one or more adhesives or cohesives formed on the attachment zone 104 and/or on the backside of the housing 202. Such connectors can further include one or more mechanical fasteners, including strap-based fasteners, hook-and-loop-fasteners, or fasteners comprising at least one button or at least one magnet. In another implementation, a pocket can be formed at or near the attachment zone 104 of the absorbent article 102 and the sensor device 106 can be inserted into the pocket. For example, some absorbent articles can be provided as pants comprising a crotch portion and a belt portion. The crotch portion and the belt portion can be joined adhesively or mechanically. In the area of adhesive joining, a certain portion can be free of adhesive and accessible from the outside. This portion can then serve as a pocket for receiving the sensor device 106. A belt, strap or other device may be used to place and hold the sensor device 106 relative to the absorbent article 102. The sensor device 106 can similarly be joined or held to an article of clothing worn by the wearer of the absorbent article.

In the embodiment shown in FIGS. 2B-2C, the sensor device 106 and the replacement sensor device 106R each include a detection unit 204 configured to detect sensory feedback data from one or more sensors 203 which may comprise any of the features or functionalities of sensors 103 described with respect to FIG. 1. In some non-limiting examples, the detection unit 204 is configured to detect optical property changes reflected in one or more indicators 112 when the sensor device is attached to the absorbent article. The detection unit 204 may include an optical sensor 206 and a light source 208 (e.g., an LED), which may be located on the backside of the sensor device 106. In accordance with these non-limiting examples, the backsheet 110 of the absorbent article can comprise a transparent or semi-transparent material that allows the detection unit 204 to view the optical property changes in the indicators 112 through the backsheet 110. Additionally, or alternatively, one or more indicators 112 can be exposed on or within a region of the backsheet 110 located directly in the attachment zone 104. The backside of the housing 202 can also include a transparent window (e.g., glass, plastic, or another suitable transparent material) or opening through which the optical sensor 206 and the light source 208 are exposed to the environment. In some implementations, the window/opening and/or the optical sensor 206 and light source 208 can further be can be hermetically sealed within the housing 202.

Some examples of optical sensors 206 are: electron tube detectors, photosensors, photomultiplier tubes, phototubes, photodetectors, opto-semiconductor detectors, photodiodes, photomultipliers, image sensors, infrared detectors, thermal sensors, illuminance sensors, visible light sensors and color sensors. Some examples of light sources 208 are: a light emitting diode (LED), organic light emitting diode (OLED), an incandescent light bulb, thermionic light emission, luminescence (e.g., among others, fluorescence, chemiluminescence, electroluminescence (e.g., LED), for emitting light onto an area, the wavelength or spectrum of which is to be assessed by the optical sensor. The optical sensor can be sensitive to visible and non-visible light. In various embodiments, ultraviolet (UV), visible infrared and near infrared wavelengths may be used.

In one or more embodiments, the optical sensor 206 can be configured to measure one or more light levels of a color strip indicator disposed within the absorbent article. In non-limiting examples, the optical sensor 206 can measure four light levels—clear, red, green and blue—with a sixteen (16) bit resolution. The clear level can correspond to a measure of an overall light intensity and the red, green and blue levels can correspond to intensity in the relevant parts of the spectrum from the color strip indicator. In this embodiment, the sensor device can take multiple measurements with the optical sensor 206. For example, in a first operation, the optical sensor 206 can be read without the light source 208 illuminated to determine a background light level. Another reading of the optical sensor 206 can also be taken in another operation with the light source 208 illuminating the color change indicator to measure the clear, red, green and blue (RGB) light levels. A difference between the two measurements is obtained in a third operation and represents a color of the color strip indicator. The clear color level can be used to normalize the RGB values. Saturation levels corresponding to one or more intermediate states of the color strip indicator can also be determined, such as from the hue, saturation and brightness (HSB) values in combination with or instead of the RGB values.

The optical sensor 206 can be spaced from the light source 208 so that direct light from the light source 208 is reduced or eliminated at the optical sensor 206. Similarly, too large a spacing between the optical sensor 206 and the light source 208 can reduce the signal strength at the optical sensor 206. The optical sensor 206 can be spaced at least about 5.0 millimeters (mm), or at least about 8.0 mm, or at least about 10.0 mm, or from about 5.0 to about 20.0 mm, or from about 10.0 to about 15 mm from the light source 208, reciting for each range every 1 mm increment therein.

In addition to spacing between the optical sensor 206 and the light source 208, other factors may also affect light level measurements of the optical sensor 206. For example, temperature, location of the sensor device 106 on the article, the type, material and color of a connector (e.g., adhesive, tape, hook and loop, strap and other materials) disposed between the sensor device and the indicator, orientation of the sensor device 106 relative to the indicator, orientation of transmit and receive windows of the sensor device 106 and the article, force of application of the sensor device 106 against the article, ambient light, position of an attachment zone 104 and position of the sensor device 106 relative to the indicators 112 within the article (e.g., in a cross-direction) such that the optical sensor 206 detects other portions of the article disposed near the indicators 112.

The size, shape, and/or dimensions of the housing 202 can vary. In some implementations in which the sensor device 106 is designed to be removably attached to disposable diapers, for safety (so as to not become a choking hazard) and convenient handling, the housing 202 can have a length (L) of at least 1.0 centimeters (cm), 2.0 cm, 3.0 cm, 4.0 cm or more (but normally less than 15.0 cm), a width (W) of least 1.0 cm, 2.0 cm, 3.0 cm or more (but normally less than 15.0 cm), and a height (H) of at least 0.5 centimeters, 1.0 cm, 2.0 cm, 3.0 cm, 4.0 cm or more (but normally less than 15.0 cm).

The material employed for the housing 202 can also vary. In some implementations, the housing 202 can be formed with a rigid material (e.g., a rigid plastic). In other implementations, the housing 202 can be formed with a flexible or partially flexible material. To be flexible, the sensor device 106 can incorporate flexible electronic components (and boards). Some suitable materials for the housing 202 can include but are not limited to, silicon, plastic, a thermoplastic, a thermoplastic elastomer (TPE), a confection, a thermosetting polymer, rubber, and the like.

Figure 3A:
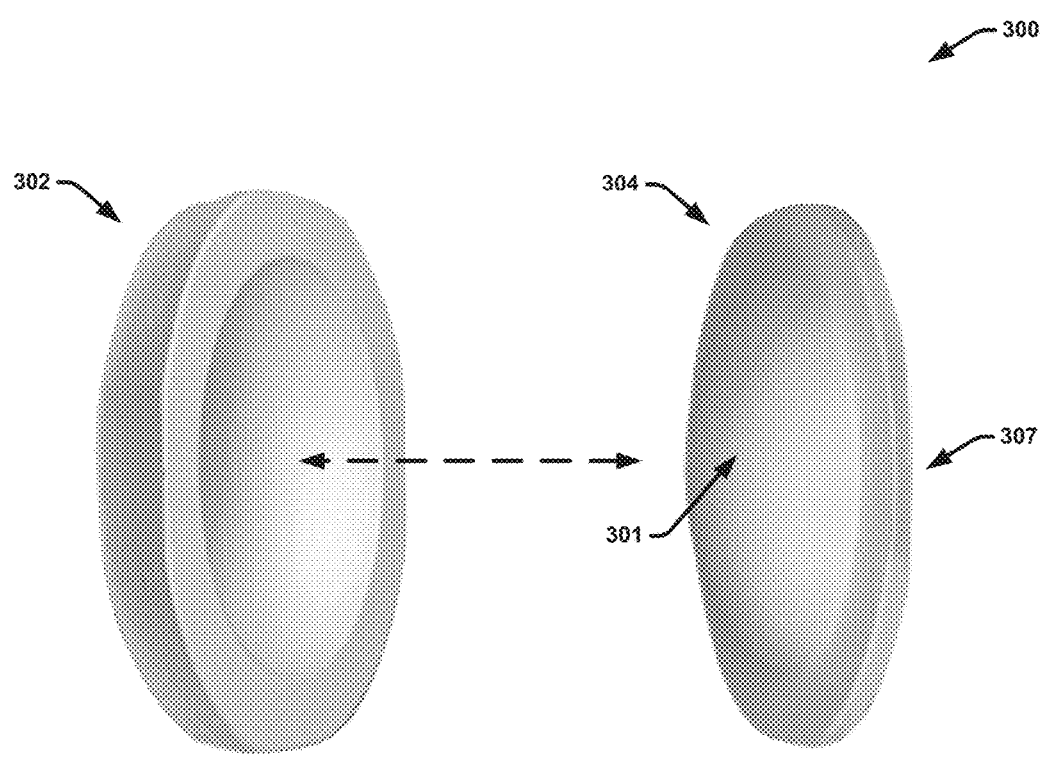
FIGS. 3A and 3B illustrate an example fabrication process for forming a sensor device with a fused outer cover elastomer formed around internal electrical components in accordance with one or more embodiments of the disclosed subject matter.
Figure 3B:
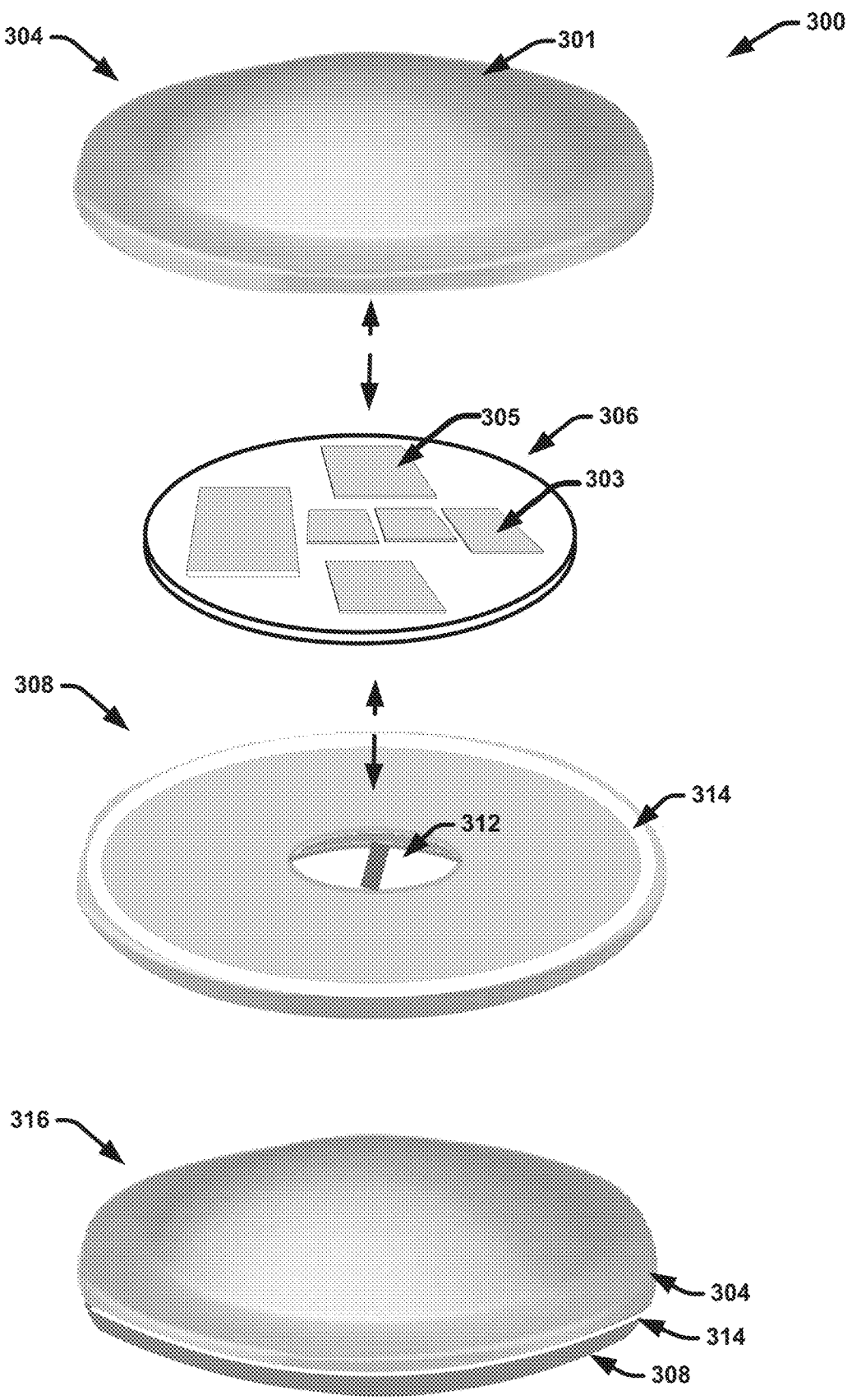

In some embodiments, the housing 202 can be or include an outer cover formed around the power unit that cannot be removed without damaging the outer cover. FIGS. 3A and 3B illustrate an example fabrication process 300 for forming a sensor device 316 with a fused outer cover formed around internal electrical components in accordance with one or more embodiments. In various embodiments, the sensor device 316 can be or correspond to sensor device 106 (including comprising component(s), sensor(s), power unit(s), housing etc. corresponding in one or more features and/or functionalities to the respective items described with respect to 106) and vice versa. In accordance with the fabrication process 300, the sensor device 316 can comprise a housing that includes a top portion 304 and a bottom portion 308 that are separately formed using one or more molds and then fused together with the electrical components inside (e.g., the power unit 305, the sensors 303, the microprocessor, the wireless communication hardware, etc.).

In this regard, FIG. 3A depicts formation of the top portion 304 of the housing using an exemplary proprietary mold 302 shown in the form of a hollow oval shape. In non-limiting examples, the top portion 304 of the sensor device housing can be formed using TPE or a similar material using injection molding or another suitable molding technique and mold 302. In accordance with these examples, the backside 303 of the top portion 304 is hollow while the external surface 301 protrudes outward away from the backside 307. However, it should be appreciated that the shape of the top portion 304 of the housing and the corresponding mold 302 can vary. In some implementations, the mold 302 can incorporate a proprietary shape and/or design. For example, the mold 302 can include a decorative design element, a symbol, a trademark, or the like, for imprinting on the external surface 301 of the top portion 304 of the housing.

FIG. 3B depicts formation of the sensor device 316 by fusing the top portion 304 of the housing to the bottom portion 308 of the housing with electrical components 306 formed inside. The material of the bottom portion 308 can include a same or similar material as the top portion 304 or a different material. In this regard, the bottom portion 308 of the housing can include a planar or substantially planar substrate upon which various electrical components 306 are formed or otherwise attached. For example, the electrical components 306 can include (but are not limited to) a power unit 305 (e.g., a non-rechargeable battery), one or more sensors 303, a microchip, wireless communication hardware, and the like. In some implementations, the electrical components 306 can be formed on a printed circuit board (PCB) which can further be attached to the bottom portion 308. In other implementations, the electrical components 306 can be formed directly on the surface of the bottom portion 308. The bottom portion 308 can further include a window 312, wherein one or more optical sensors 206 and/or a light source 208 can be aligned with the window 312 when formed on the bottom portion 308.

In various embodiments, the top portion 304 can be attached to the bottom portion 308 with the electrical components 306 formed inside the hollow area of the backside 307 of the top portion 304 to generate sensor device 316. The mechanism for attaching the top portion 304 to the bottom portion can vary. However, in various exemplary embodiments, the mechanism for attaching the top portion 304 and the bottom portion 308 can result in fusing the respective portions to one another in a manner that prevents separation of the respective portions without physically damaging either portion. For example, the top portion 304 can be fused with the bottom portion 308 (e.g., using a bonding material/mechanism, using a permanent adhesive, or the like) in a manner such that removal of the power unit or any other electrical components from inside renders the top portion 304 and/or the bottom portion 308 unusable with another power unit and/or with one or more other electrical components.

In one exemplary embodiment, as shown in FIG. 3B, a fusing material 314 can be formed around the perimeter of the bottom portion and used to fuse the top portion 304 to the bottom portion 308. The fusing material 314 can vary depending on the material used for the top portion 304 and the bottom portion 308. For example, in some implementations, the fusing material 314 can comprise an adhesive (e.g., an epoxy a curable epoxy, a structural acrylic adhesive, a cyanoacrylate adhesive, an ultraviolet light curable adhesive, etc.). In other implementations, the top portion 304 can be fused with the bottom portion 308 using extruded-bead sealing, friction welding, high frequenting welding, hot gas welding, laser welding, solvent welding, spin welding, ultrasonic welding, or soldering. In some implementations, the sensor device 316 can be made water resistant and the housing (e.g., including the top portion 304 fused to the bottom portion 308) can hermetically seal the internal electrical components therein.

Figure 4:
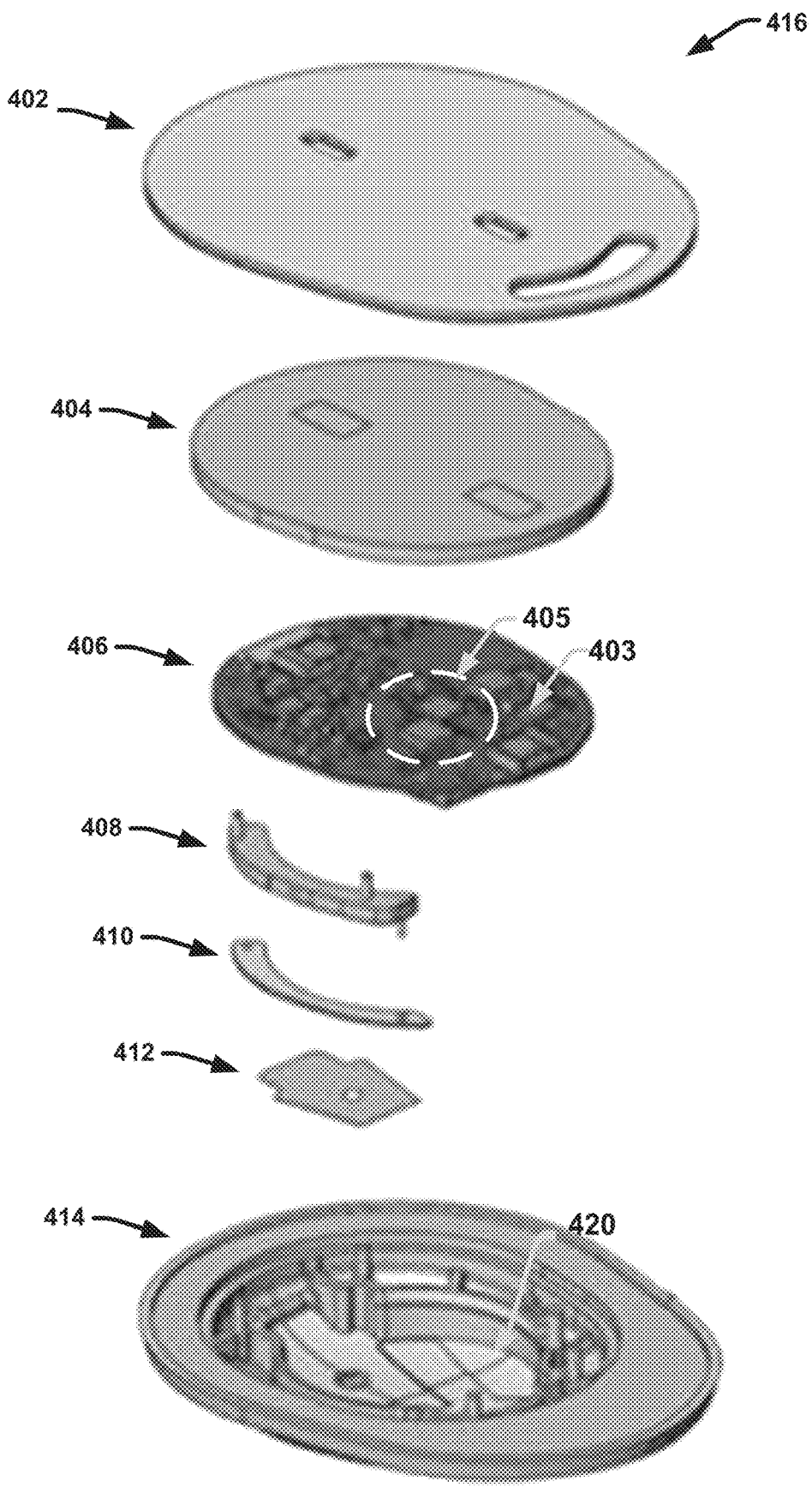
FIG. 4 illustrates a dissembled view of an example sensor device in accordance with one or more embodiments of the disclosed subject matter.

FIG. 4 illustrates a dissembled view of an example sensor device 416 showing the relative arrangement of various parts of the sensor device. In various embodiments, disassembled sensor device 416 shown in FIG. 4 can be or correspond to sensor device 106 and/or sensor device 316 (including comprising component(s), sensor(s), power unit(s), housing etc. corresponding in one or more features and/or functionalities to the respective items described with respect to 106 and/or 316) and vice versa. In the embodiment shown, the sensor device includes a lower housing portion 404 and an upper housing portion 414 that can be fused together (e.g., using ultrasonic welding) with various internal components formed therein. With reference to FIG. 3B, in some implementations, the lower housing portion 404 can be or correspond to the bottom portion 308, and the upper housing portion 414 can be or correspond to the top portion 304. In various embodiments, the lower housing portion 404 and/or the upper housing portion 414 can be made of hard plastic material, such as Tritan or polycarbonate.

The internal components can include (but are not limited to): a PCB 406, an antenna standoff 408, an antenna 410, and an LED mask 412. The power unit 405 (e.g., a non-rechargeable battery), one or more sensors 403 and other electrical components (if any) can be placed on the PCB 406. In this regard, the power unit can be encapsulated inside a welded housing that consists of the lower housing portion 404 and the upper portion 414. The housing portions 404, 416 may be ultrasonically welded together. In some implementations, the external surface of the upper housing portion 414 (or the entire housing) can be wrapped in an elastomer 420. As noted above, one or both of the housing portions 404 and 414 and/or the elastomer 420 can be formed about the PCB such that removal of the power unit or any other electrical components from inside renders the housing or portion thereof unusable with another power unit and/or with one or more other electrical components. In the embodiment shown, an attachment component 402 can be formed on the lower housing. The attachment component 402 may facilitate attaching the sensor device to the absorbent article. For example, the attachment component 402 can include a piece of Velcro™, and/or the various other attachment devices described above.

Figure 5:
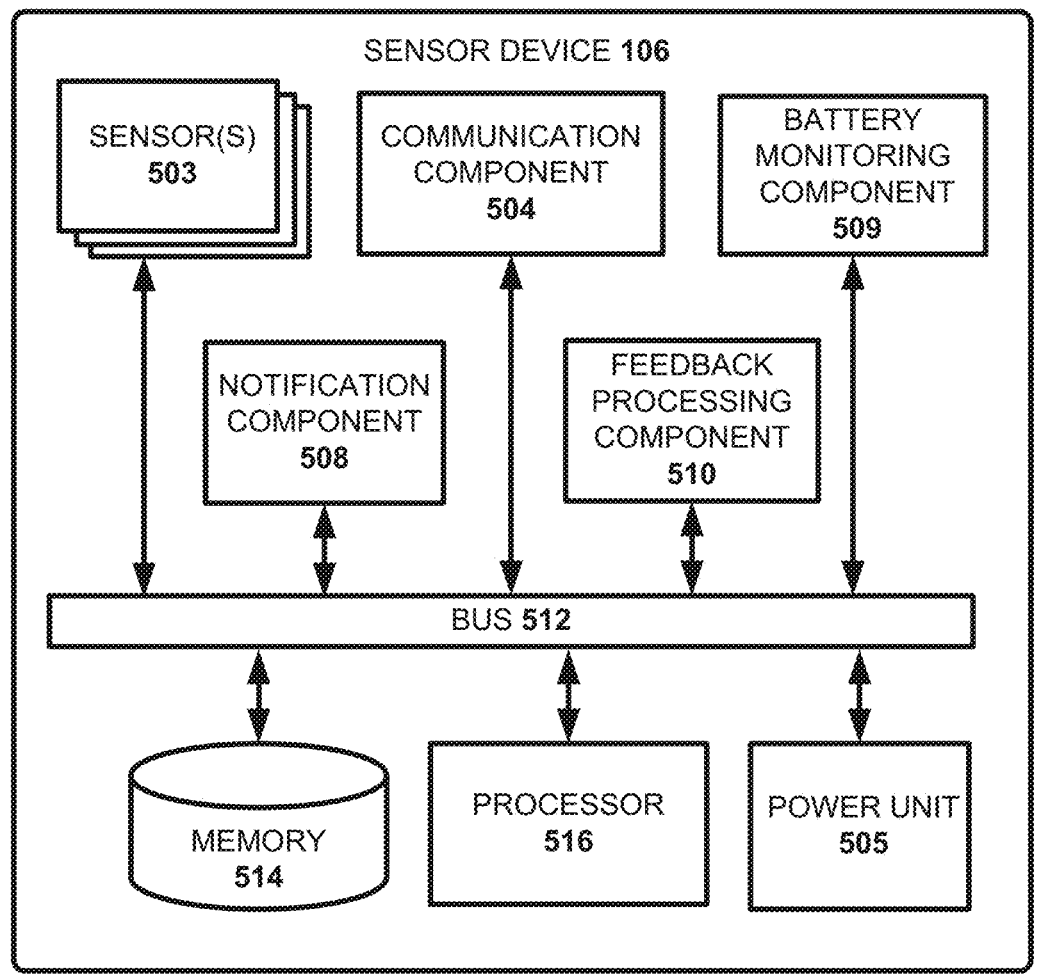
FIG. 5 illustrates a block diagram of an example sensor device in accordance with one or more embodiments of the disclosed subject matter.

FIG. 5 illustrates a block diagram of an example sensor device 106. Various aspects of devices, systems, apparatuses or processes explained in this disclosure can constitute machine-executable component(s) embodied within machine(s), (e.g., embodied in one or more computer readable mediums associated with one or more machines). Such components, when executed by one or more machines (e.g., computers, computing devices, virtual machines, etc.), can cause the machines to perform the operations described.

For example, in the embodiment shown, the sensor device 106 can include one or more sensors 503, communication component 504, battery monitoring component 509, notification component 508 and feedback processing component 510. The sensor device 106 can also include at least one memory 514 configured to store computer executable components and instructions (e.g., the communication component 504, the battery monitoring component 506, the notification component 508, the feedback processing component 510, etc.). The sensor device 106 can also include at least one processor 516 (e.g., a microprocessor) to facilitate operation of the computer executable components and instructions by the sensor device 106. The sensor device 106 can further include a power unit 505 that provides for powering the various electrical components of the sensor device 106. In various embodiments, the sensor device 106 can incorporate a non-rechargeable battery as the power unit 505. However, other suitable type of power sources/units are envisioned.

The sensor device 106 can further include a device bus 512 that couples the various components of the sensor device 106, including, but not limited to: the sensors 503, the communication component 504, the battery monitoring component 509, the notification component 508, the feedback processing component 510, the memory 514, the processor 516 and the power unit 505.

The sensor device 106 can include one or more sensors 503 formed on or within a housing of the sensor device (e.g., housing 202) that are configured to sense, detect or otherwise capture sensor data regarding usage of an absorbent article to which the sensor device is designed to be attached and/or activity of the wearer. The sensor(s) 503 can be or include any of the features and functionalities of the sensors 103, 203 described above and vice versa. For example, as discussed with reference to FIGS. 1, 2A and 2B, the sensors 503 can include one or more image sensors, optical sensors, chemical sensors, biosensors, a biochemical sensors, temperature sensors, force/pressure sensors, motion sensors (e.g., an accelerometer, a gyroscope, etc.), humidity sensors, acoustic sensors, an RFID reader/sensor, and combinations thereof.

The communication component 504 can provide for communicatively coupling the sensor device 106 with devices external to the sensor device (e.g., one or more external user devices 108, computing device 118, and/or various other devices physically remote from sensor device 106). In this regard, the communication component 504 can include software, hardware, or a combination of software and hardware that is configured to facilitate performance of wireless (and/or wired) communications between the sensor device 106 and one or more external devices. For example, the communication component 504 can include and/or be configured to control operation of one or more transmitters/receivers of the sensor device 106 to provide for transmitting information to and/or receiving information from one or more devices external to the sensor device.

The communication component 504 can be configured to facilitate wireless communication with such devices using a variety of wireless communication protocols. For example, in one or more embodiments, the communication component 504 can communicate with an external device using a Bluetooth® communication protocol, a near-field communication (NFC) protocol, or another type of communication protocol over a PAN or a LAN, (e.g., a Wi-Fi network) that can provide for communication over greater distances than NFC protocol or that can provide various advantages (such as increased security). Other communication protocols that can be employed by communication component 504 to communicate with an external device can include, but are not limited to: a Session Initiation Protocol (SIP) based protocol, a Zigbee® protocol, a RFSCE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a cellular communications protocol (e.g., second, third, fourth and fifth Generation Partnership Project (GGP) protocols, Long Term Evolution (LTE), protocols), machine type communication (MTC) protocols, Narrowband Internet-of-things (NB-IoT) protocols, other radio frequency (RF) communication protocols, non-RF communication protocols (e.g., induction based, optical based, audio based, etc.) and/or other proprietary and non-proprietary communication protocols.

The battery monitoring component 509 can facilitate monitoring power unit replacement information, including a power level, time-in-use, age, and/or performance of the sensor device 106 or more specifically of the power unit 505. The battery monitoring component can monitor such information, or portions thereof, continuously, based on one or more predetermined schedules and/or in response to an interrogation request from an external user device 108 or computing device 118. A threshold value or other triggering condition may be stored in a memory of the respective device such that the monitored information can be compared to said threshold or triggering condition. The notification component 508 may send a notification based on the determination that the triggering condition has been met. For example, the battery monitoring component 506 can facilitate monitoring a power level of the power unit 505. A threshold power level can be predefined and stored in memory 514. The battery monitoring component 506 can further determine when the power level of the battery is near, less than or equal to the threshold power level. The notification component 508 can send a notification message to a device external to the sensor device (e.g., the external user device 108 and/or to a computing device 118 of the replacement system 116) in response to the power level determination. For example, the notification can include information indicating the current (low) power level of the sensor device and/or warning the user that the current power level is nearing, at or less than the threshold power level. In some implementations, the external user device 108 can be configured to render the notification message at the external user device (e.g., via a device display), thereby prompting the user to order a replacement sensor device. In other implementations, as discussed in greater detail infra with reference to FIG. 5, the external user device 108 and/or an application associated with the external user device 108 can automatically order and/or initiate ordering the replacement sensor device based on receipt of the notification message from the sensor device 106.

Further to the above, the battery monitoring component 509 can be configured to report the current power level of the sensor device 106 to the external user device 108 and/or computing device 118 in accordance with a defined scheduled, in association with reporting sensory feedback data, and/or in response to receipt of an interrogation request from the external user device 108 and/or computing device 118. For example, in some implementations, the battery monitoring component 509 can be configured to check the power level of the power unit according to a defined schedule (e.g., every N minutes, every M hours, once a day, etc.) and report the current power level to the external user device as a power level status update message. In another non-limiting example, the battery monitoring component 509 can be configured to include information identifying the current power level of the sensor device 106 when reporting captured sensor measurements and/or sensory feedback data determined based on the sensor measurements. Still in another implementations, the battery monitoring component 509 can be configured to provide the current power level of the sensor device to the external user device 108 and/or computing device 118 based on receipt of an interrogation request from the external user device 108 and/or the computing device 118. With these embodiments, the external user device 108 and/or computing device can determine if the reported power level of the sensor device 106 is near, at or below the threshold power level. In such instances, the threshold power level may be stored in a memory of the respective device(s).

The sensor device 106 can also include feedback processing component 510 to facilitate processing raw sensor data captured via one or more sensors 503. The sensor data can include any measurements, properties, characteristics mentioned above with respect to sensory data and feedback. In some embodiments, the sensor device 106 can be configured to send some or all of the sensor data (e.g., raw sensor data and/or digital information corresponding to captured/detected sensor measurement values) to an external user device 108 for processing and/or presentation by the external user device 108. The external user device 108 can be configured to process and analyze some or all sensor data to determine and/or infer feedback data based on captured sensor measurements as discussed above.

Additionally, or alternatively, the feedback processing component 510 can be configured to provide for partial and/or full onboard processing of the sensor data to generate sensory feedback data based on the captured sensor data. For example, in various embodiments, the feedback processing component 510 can be configured to process/analyze some or all sensor data captured via one or more sensors using predefined processing logic (e.g., algorithms, heuristics, machine learning models, defined correlations, tracked data correlations, etc.) to determine and/or infer feedback information regarding usage of the absorbent article and/or activity of the wearer.

For example, in one or more implementations, an optical sensor of the sensor device 106 can detect and/or determine one or more RGB light levels or HSB levels of a color strip indicator provided within the absorbent article. The feedback processing component 510 can further determine and/or infer sensory feedback data regarding usage (e.g., presence, absence and/or amount of one or more bodily exudates, and/or a local saturation), based at least in part on the RGB light level or HSB level information as captured/generated by one or more sensors 503. In another example, sensors 503 can include sensors that capture activity data (e.g., motion sensors), and the feedback processing component 510 can be configured to process the activity data to determine sensory feedback information regarding activity levels and/or patterns of the wearer. In some implementations, the feedback processing component 510 can further provide for determining and/or inferring additional information regarding the behavior of the wearer, and/or the physiological and/or health status of wearer based on the captured sensor data (e.g., detected properties of the bodily exudates, timing and frequency of the bodily exudates, activity level/patterns of the wearer over time, and/or various other captured and/or tracked parameters).

In some implementations, the communication component 504 can be configured to send the sensory feedback information to the external user device 108 for rendering and/or further processing by the external user device 108 and/or forwarding to the replacement system 116 (or another device). The external user device 108 can further be configured to present or otherwise provide the determined information to the user as a real-time notification (e.g., notification when diaper is wet), as an assessment report, or the like.

In various implementations, the notification component 508 can be configured to generate and send notifications to the external user device 108 based on detection of defined sensor measurement values and/or based on a determination, by the feedback processing component 510, that a defined event or condition has occurred as determined based on the sensor data. By way of non-limiting example, the notification component 508 can be configured to generate and send the external user device 108 a notification that the absorbent article is wet based on a determination that the absorbent article is wet or has reached a defined saturation level. In another non-limiting example, the notification component 508 can generate and send the external user device 108 a notification that wearer has woken based on a determination that the wearer's activity level/pattern indicates the wearer is no longer asleep.

In some embodiments, the notification component 508 can further be configured to provide notifications regarding connectivity issues and/or calibration issues associated with the power unit of the sensory device 106. For example, the battery monitoring component 509 can be configured to determine if a connectivity issue or calibration issue exists in association with initial insertion of the power unit into the sensor device. The battery monitoring component 509 can also periodically check the power unit's status over use of the sensor device for possible connectivity and/or calibration issues. The notification component 509 can further provide a notification in response to detection of a connectivity and/or calibration issue. The notification component 509 can send the notification to the external device 108 and/or the sensor device replacement system 116. The external device 108 and/or the sensor device replacement system 116 can further render or otherwise present the notification to the device/system user. For example, the notification can include a visual and/or audible notification rendered at the sensor device itself (e.g., a blinking light, a beeping noise, etc.).

Figure 6:
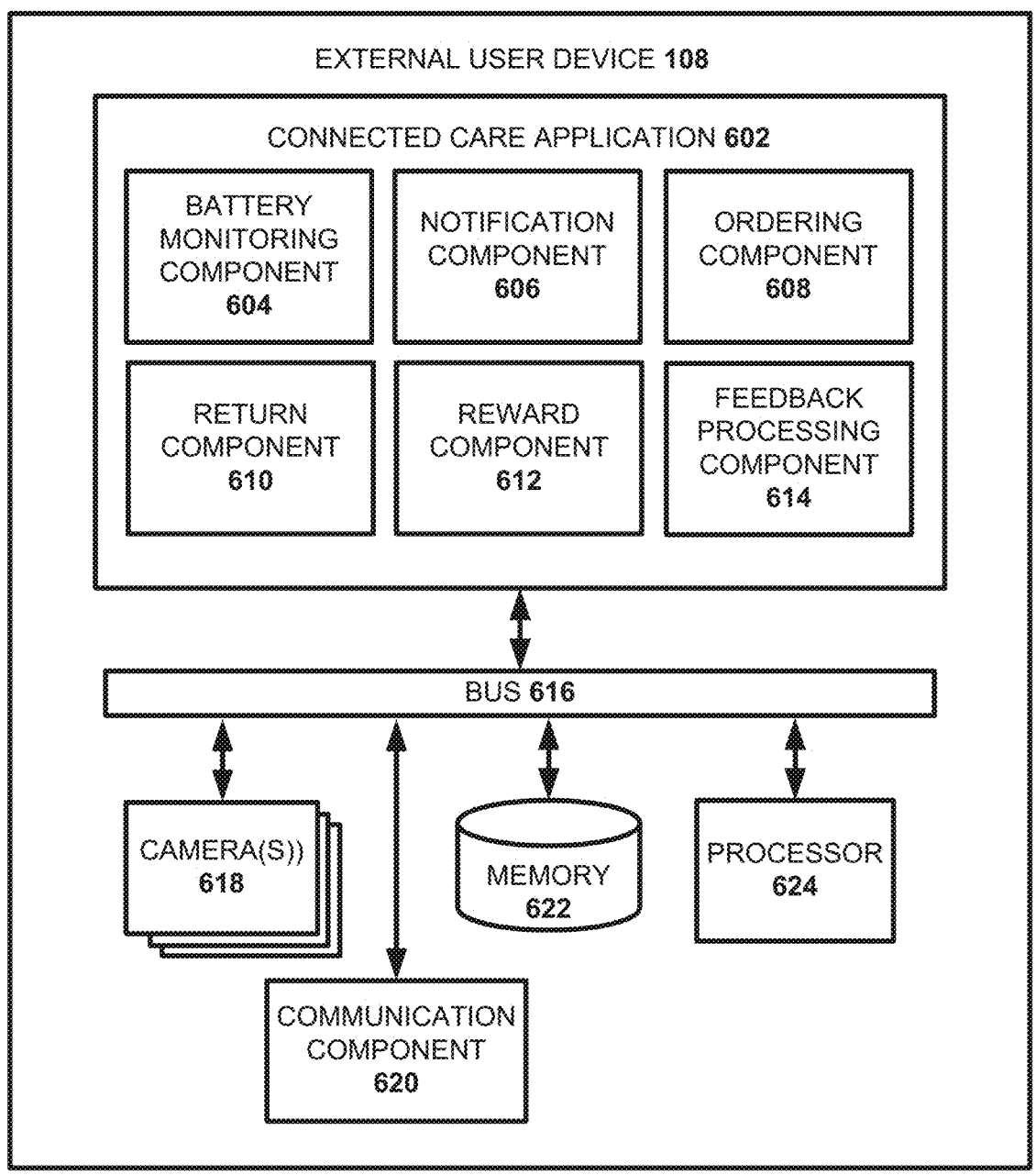
FIG. 6 illustrates a block diagram of an example external user device that facilitates replacing battery depleted sensor devices designed to be reused with absorbent articles in accordance with one or more embodiments of the disclosed subject matter.

FIG. 6 illustrates a block diagram of an example external user device 108 that facilitates replacing sensor devices, and/or power units for use in sensor devices, that are designed to be reused with absorbent articles. In the embodiment shown, the external user device 108 can include various computer executable components associated with a connected care application 602 executed by the external user device 108. The connected care application 602 can include a dedicated client application, a web-application, a thin client application, a hybrid application, or the like. In this regard, the connected care application 602 can provide various online features and functionalities associated the sensor device 106 in association with communication with at least one external system, such as replacement system 116, and other suitable networked service providers (e.g., a cloud-based server device, edge-based system, an application server, and the like). Additionally, or alternatively, one or more features and functionalities of the connected care application 602 can be performed offline.

In addition to the connected care application 602, the external user device 108 can include one or more cameras 618, a communication component 620, at least one memory 622, at least one processor 624 and a device bus 616. It should be appreciated that in some embodiments, one or more of these components can be removed from the external user device 108. Further, one or more of these components shown in FIG. 6 can executed by the sensor device 106 and/or the computing device 118. In various embodiments, the memory 622 can be configured to store computer executable components and instructions (e.g., the connected care application 602 and/or one or more components of the connected care application 602). The external user device 108 can also include at least one processor 624 to facilitate operation of the computer executable components and instructions by external user device 108. The external user device 108 can further include a device bus 616 that couples the various components of the external user device 108, including, but not limited to, the connected care application 602, the camera 618, the communication component 620, the memory 622 and the processor 624.

In the embodiment shown, the connected care application 602 can include battery monitoring component 604, notification component 606, ordering component 608, return component 610, reward component 612, and feedback processing component 614. In various embodiments, the notification component 606, the feedback processing component 614 and the communication component 620 can include any of the features and functionalities as that described with the corresponding components shown in FIG. 5 (e.g., notification component 508, feedback processing component 510 and communication component 504, respectively). Repetitive description of like elements employed in respective embodiments is omitted for sake of brevity.

In various embodiments, the battery monitoring component 604 can comprise any of the features and functionalities as battery monitoring component 509, or complementary features and functionalities. For example, in some embodiments in which the sensor device 106 is configured to notify the external user device 108 when its power unit is nearing, at or below a threshold level, the battery monitoring component 604 (and/or the notification component 606) can be configured to receive the notification. Based on receipt of the notification, the notification component 606 can further render the notification at the external user device 108 and/or the battery monitoring component 604 can direct the ordering component 608 to order or initiate ordering a replacement sensor device (e.g., with the replacement system 116).

Additionally, or alternatively, the sensor device 106 may report its current power unit replacement information (e.g., current power level, current time in use, current performance), and the battery monitoring component 604 can be configured to evaluate the information reported by the sensor device and determine whether said information is nearing, less than or equal to a threshold level and/or whether it otherwise meets a triggering condition. The sensor device 106 can be configured to regularly report its current power level in accordance with a defined schedule, with reported sensor measurements, with reported feedback data, or the like. Additionally, or alternatively, the battery monitoring component 604 can ping (e.g., interrogate) the sensor device and/or direct the sensor device 106 to report current power unit replacement information. With these embodiments, the notification component 606 can be configured to generate a notification based on a determination, by the battery monitoring component 604, that the power unit is nearing, at or below a given threshold or otherwise meeting a triggering condition (e.g., the power level is less than the threshold power level, the performance is less than the threshold performance level). In some implementations, the notification component 606 can further render the notification at the external user device 108 (e.g., for presentation to the device user). In other implementations, the notification component 606 can direct the ordering component 608 to order or initiate ordering a replacement sensor device (e.g., with the replacement system 116) based on generation of the notification and/or based on a determination that the power unit and/or sensor device is near, at or less than a given threshold or meets a triggering condition.

In this regard, with reference to the connected care application 602 in view of FIG. 1, the ordering component 608 can facilitate ordering a replacement sensor device with the replacement system 116 based on receipt of (e.g., from the sensor device 106) and/or generation of (e.g., by the notification component 606) a notification message indicating that power unit requires or will soon require replacement. The ordering component 608 can further interface with the computing device 118 and/or the inventory unit 120 and automatically order a replacement sensor device 106R that corresponds to the sensor device currently being used. For example, in some embodiments, the ordering component 608 can generate a replacement order request that includes information identifying or indicating the sensor device to be replaced. For instance, the replacement order request can identify or indicate the type of the sensor device to be replaced, the make and model of the sensor device to be replaced, the serial or identification number for the sensor device to be replaced, the size and/or location of the power unit, and the like. The replacement order request can also include information identifying or indicating an address for mailing the replacement sensor device to the customer and/or financial information used to pay for and fulfill the order. The ordering component 608 can further send the replacement order request to the replacement system 116 for fulfilment by the replacement system 116. In this regard, based on generating and/or sending the replacement order request, a replacement sensor device can be sent to the customer associated with the request at an address associated with the order.

In some embodiments, the ordering component 608 can automatically gather such replacement order information (e.g., describing the type of sensor device to be replaced, providing the delivery address, providing the financial payment information, etc.) from a user account that the user has established with the connected care application 602 and/or the replacement system 116. For example, in some embodiments, a user can establish a secure user account with the connected care application 602 and/or replacement system 116 that identifies information about the user, includes product usage/purchase history information, includes authorization information for automatic ordering of replacement sensors devices, includes delivery preferences for delivering the replacement sensor devices, and the like. The user account information can also include information identifying the current sensor device to be replaced, including information identifying or indicating the make/model of the current sensor device, the type of power unit employed, the timing/duration of usage, and the like.

Additionally, or alternatively, the ordering component 608 can receive user input in association with generating a replacement order request and/or sending the replacement order request to the replacement system 116. For example, in some implementations, based on the system's analysis of power unit replacement information, the notification component 606 can generate a prompt that can be rendered at the external user device 108. The prompt can include an interactive prompt that facilitates receiving user input relevant to ordering and receiving a replacement sensor device. For example, the prompt can ask the user if he/she would like to order a replacement sensor device, require the user to provide input authorizing or denying placement of the order, ask for information regarding the sensor device to be replaced and/or ask for information necessary for payment and/or shipment. In non-limiting examples, the ordering component 608 can facilitate generating the replacement order based on receipt of user input authorizing ordering of the replacement sensor device via the prompt. Further, if relevant information regarding the type of sensor device to be replaced, the location for shipping the replacement and the customer's payment information for purchasing the replacement sensor device (e.g., when applicable) has not already been received, the ordering component 608 can prompt the user to provide the relevant information. In some implementations, the ordering component 608 can prompt the user to take and provide a picture (e.g., using the camera(s) 618) of the used sensor device to be replaced. This picture may be included in the replacement order request to facilitate identifying the used sensor device and determining an appropriate make and model for the replacement sensor device.

The return component 610 can further facilitate returning used, damaged or depleted sensor devices back to the refurbishment unit 122 for refurbishment by the replacement system 116 (and/or to prevent refurbishment by an unauthorized entity). For example, in one implementation, the return component 610 can provide the customer with delivery instructions, labeling and/or packaging material to facilitate returning the used sensor device to the replacement system 116. For instance, the return component 610 can provide the consumer with the delivery instructions, labeling (e.g., a return QR code or bar code), packaging material etc., for returning the used sensor device in association with sending the consumer the ordered replacement sensor device, receiving a replacement order and/or receipt of an input authorizing a replacement order. In some embodiments, the reward component 612 can further be configured to issue a reward to a user account associated with the sensor device 106 and/or external user device 108 based on at least one of ordering the replacement sensor device with the replacement system 116, authorizing a replacement order, purchasing a replacement, and/or returning the used/depleted sensor device to the replacement system. Rewards can include a coupon, a discount, a credit, reward points, free shipping, additional features on the connected care application, ancillary services, products and combinations thereof.

As noted, the feedback processing component 614 may comprise any of the features and functionalities of the feedback processing component 510. The feedback processing unit may determine sensory feedback information based on received sensor data provided by the sensor device 106. Additionally, or alternatively, the feedback processing component 614 of the external user device can further receive additional inputs, such as but not limited to: information regarding sensor device (e.g., date of purchase), the time the absorbent article was attached to a wearer, time the sensor device was attached to the absorbent article, the current time, wearer information (e.g., demographic information such as sex, age, weight of wearer, biometric information of the wearer, whether the wearer is toilet training, degree of wearer incontinence), caregiver preference information, temperature, humidity and/or ambient sensor information. The feedback processing component 614 may use these additional inputs separately and/or in combination with the information received from the sensor device.

With these embodiments, the feedback processing component 614 can determine a predicted status of the absorbent article, power unit and/or sensor device based at least in part upon the sensor data received from the sensor device 106 and contextual information (e.g., wear time of the diaper and baby demographic information). Contextual information, for example, can be input by consumers, retrieved via other sensors or information sources (e.g., thermostats). The sensor data, for example, can include time-in-use, and the input can include date of purchase. The feedback processing component can determine the status of the power unit, for example, with one or more functions incorporating the captured sensor data and user inputs.

The notification component 606 can report the status of the absorbent article, power unit and/or sensor device, for example, to a user to indicate a percent or other indication remaining capacity for displaying at the external user device 108. In one particular implementation, for example, the external user device 108 can display a graphical or numerical representation of the status of the absorbent article or the sensor device. Additionally, or alternatively, the notification component may be configured to generate a notification based on information received from a computing device 118, such as the information described in detail below. In non-limiting examples, the notification component can generate a notification that an order is complete and/or received based on a determination of such by the order processing component 706. In further nonlimiting examples, the notification component can generate a notification that a replacement has shipped, and optionally the address to which it was shipped, and/or that it has been delivered based on a determination by the order processing unit.

Figure 7:
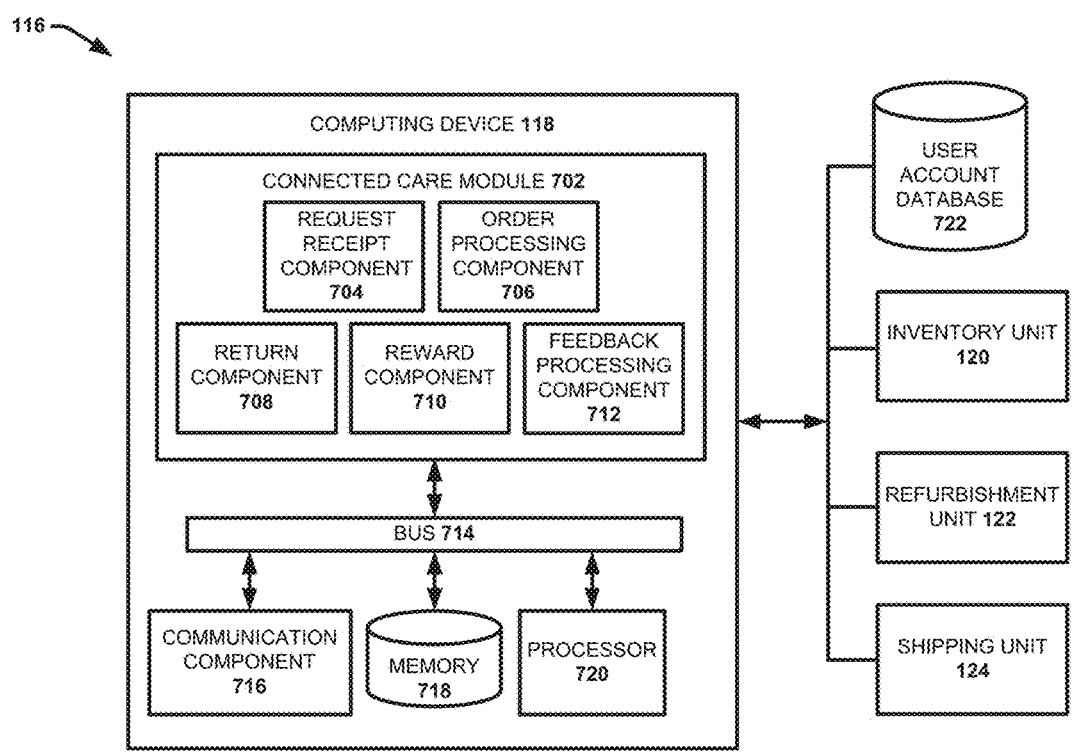
FIG. 7 illustrates a block diagram of an example replacement system that facilitates replacing battery depleted sensor devices designed to be reused with absorbent articles in accordance with one or more embodiments of the disclosed subject matter.

FIG. 7 illustrates a block diagram of an example replacement system 116 that facilitates replacing sensor devices, and/or power units for use in sensor devices, that are designed to be reused with absorbent articles. In the embodiment shown, the replacement system 116 can include at least one computing device 118, inventory unit 120, refurbishment unit 122 and shipping unit 124. Repetitive description of like elements employed in respective embodiments is omitted for sake of brevity. The replacement system 116 can also include a user account database 722 including account information for customers that have previously received and/or used in one or more connected care system products (e.g., sensor devices, absorbent articles, the connected care application 602 and the like). For example, the user account database 722 can include information identifying users (e.g., username/password, home address, contact information etc.), their product purchase and/or usage history, current product information (e.g., current sensor device identifier and attributes), membership subscriptions (e.g., for automatic delivery of replacement sensor devices), billing information, shipping address information, and combinations thereof.

In the embodiment shown, the computing device 118 can include various computer executable components associated with a connected care module 702 executed by the computing device 118. The computing device 118 can further include at least one memory 718 to store computer executable components and instructions (e.g., the connected care module 702 and/or one or more components of the connected care module 702). The computing device 118 can also include at least one processor 720 to facilitate operation of the computer executable components and instructions by computing device 118. An external server device, a cloud-based system, and/or an edge-based system may comprise the processor. The computing device 118 can also include a communication component 716. The communication component 716 can include any of the features and functionalities of the communication component 620. The computing device 118 can further include a device bus 714 for communicatively coupling the respective components of the computing device (e.g., the connected care module 702, the communication component 716, the memory 718 and the processor 720). Repetitive description of like elements employed in respective embodiments is omitted for sake of brevity.

In some embodiments, the connected care module 702 can include the same or similar components as the connected care application 602 and vice versa. For example, the connected care module 702 can include a return component 708, a reward component 710 and a feedback processing component 712 that can respectively provide any of the features and functionalities of, or complementary features and functionalities to, the return component 610, reward component 612 and feedback processing component 614. For example, in some implementations, the return component 708 can facilitate managing returns of used or depleted sensor devices to the refurbishment unit. For instance, the return component 708 can generate return labeling information for the return of the used sensor devices, and track product returns in association with interfacing with the shipping unit 124 and the refurbishment unit 122. The reward component 710 can also manage issuing rewards to users and their corresponding user accounts (e.g., as provided in the user account database 722). For example, the reward component 710 can receive information from the return component 708 confirming return of a used or depleted sensor device. Based on the confirmation of the return, the reward component 710 can be configured to issue a reward to the corresponding user account. Additionally, or alternatively, the reward component 710 can be configured to issue (e.g., issued to their user accounts) or otherwise provide customers with rewards based on participation in an automatic sensor device replacement program, receipt of order authorization information authorizing an order for a replacement sensor device, receipt of purchase information confirming purchase of a replacement sensor device, and the like. The reward can include a coupon, a discount, a credit, reward points, free shipping, additional features on the connected care application, ancillary services, products and combinations thereof.

The connected care module 702 can also include a request receipt component 704 and an order processing component 706 to facilitate ordering and replacing sensor. In this regard, in various embodiments, the request receipt component 704 can be configured to receive replacement sensor device order requests from external user devices 108. For example, in some implementations, the request receipt component 704 can receive requests to replace and/or refurbish a used, broken, power depleted and/or lost sensor device, wherein the requests are generated and/or sent by the external user device 108 using the ordering component 508. In this regard, in some implementations, the request receipt component 704 can automatically receive a request to replace a sensor device 106 based on a determination (e.g., by the sensor device 106 using battery monitoring component 509 and/or by the external user device 108 using battery monitoring component 604) that a triggering condition has been met (e.g., power level of the sensor device is below a threshold power level).

The order processing component 706 can further facilitate processing the received order requests and shipping of a replacement sensor device to the customer associated with the order request at an address associated with the order request. In this regard, in various embodiments, the received request can include or otherwise be associated with attribute information identifying or indicating one or more attributes of the sensor device to be replaced/refurbished. For example, in some embodiments, the attribute information can identify or indicate a type of the sensor device, a make and model of the sensor device, a device identifier for the sensor device (e.g., a unique number or name), and the like. The attribute information can also include information regarding the power unit employed by the used sensor device (e.g., type, voltage, size, etc.) and/or the current power unit replacement information (e.g., power level, age, time-in-use) at the time when the request was made. As described with reference to FIG. 6 and the ordering component 604, in some implementations, this attribute information can be extracted from the account information associated with a user providing the request. In other implementations, some or parts of this attribute information can be received as manual input in association with completing a replacement order request using the connected care application 602. In another implementation, the request can include an image/picture of the used sensor device and the order processing component 706 can determine the corresponding attribute information based on analysis of the image/picture. For example, the order processing component 706 can employ various types of automated image analysis pattern recognition techniques to determine information regarding a type, make, model etc., of the sensor device reflected in the image/picture. In some implementations, the sensor device can include a serial number and/or barcode that can be included in the picture and the order processing component 706 can read the serial number and/or barcode using text recognition software, barcode scanning software, and the like. The order processing component 706 can employ the attribute information to select a replacement sensor device for the sensor device and/or facilitate shipping the replacement sensor device to the customer.

Additionally, or alternatively, the order processing component can be configured to act only under certain circumstances. For instance, the order processing component may select the appropriate replacement and/or facilitate shipment only after a determination that fulfilment of the request is authorized. The order processing component 706 can determine that fulfilment of the order is authorized based on account information for the customer indicating that automatic fulfillment of replacement sensor devices is authorized (e.g., in association with participation in an automatic sensor device replacement subscription/program). The order processing component 706 can determine that fulfilment of the order is authorized based on receipt of confirmation of payment from the customer.

The order processing component 706 can interface with the inventory unit 120 to identify an appropriate replacement sensor device that is in stock based on the attribute information. For example, in some implementations, the order processing component 706 can select the same sensor device (e.g., same make and model) as the used/depleted sensor device. In other implementations, the order processing component 706 can select a different make and model of the sensor device that better suits the customers' needs based on analysis of product use history. The order processing component 706 can further interface with the shipping unit 124 to facilitate shipping of the replacement sensor device to an address associated with the request and/or the user account.

Figure 8:
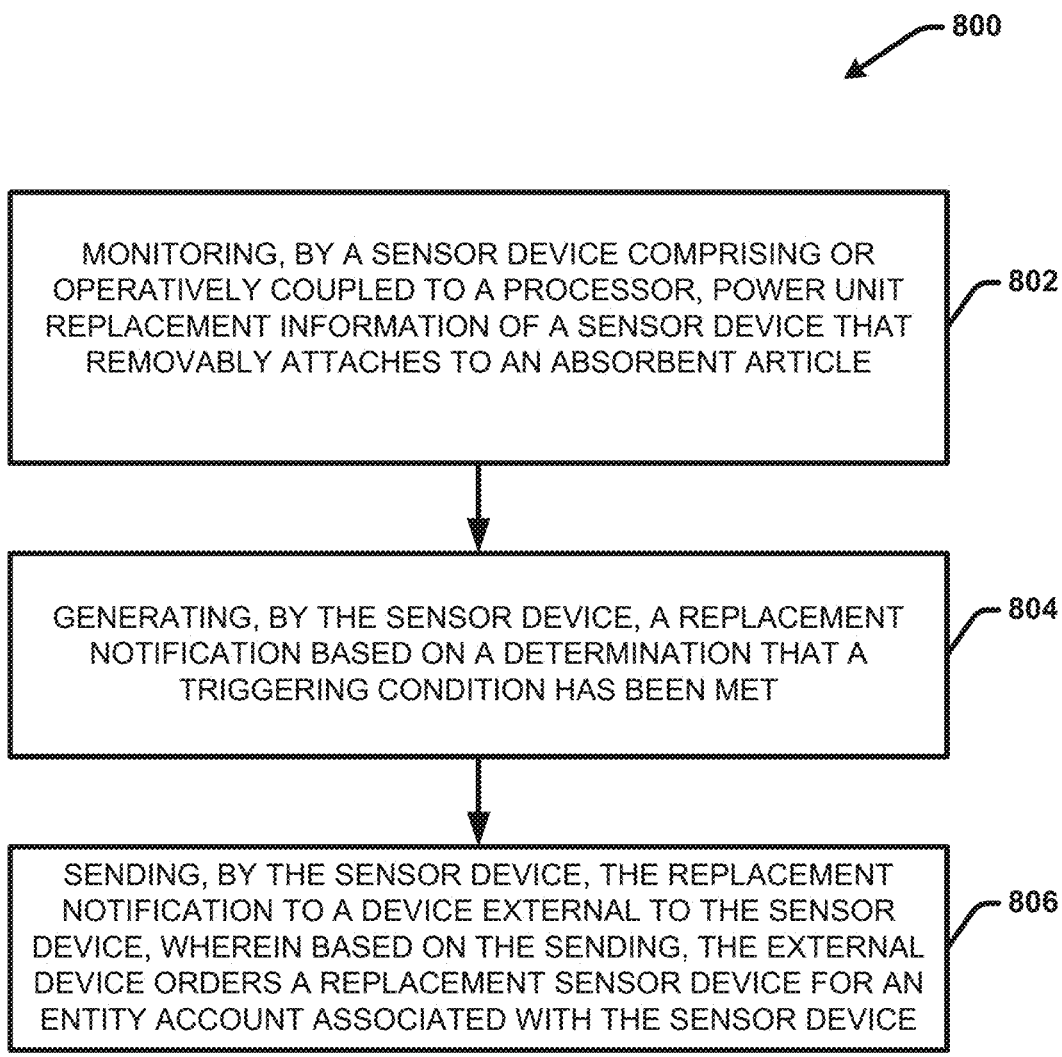
FIG. 8 presents a high-level flow diagram of an example process for replacing battery depleted sensor devices designed to be reused with absorbent articles in accordance with one or more embodiments of the disclosed subject matter.

FIG. 8 presents a high-level flow diagram of an example process 800 for replacing sensor devices, and/or power units for use in sensor devices, that are designed to be reused with absorbent articles. Repetitive description of like elements employed in respective embodiments is omitted for sake of brevity. At 802, a sensor device comprising or operatively coupled to a processor (e.g., sensor device 106, sensor device 316 and the like) can monitor a power unit replacement information (such as the power level of a non-rechargeable battery), wherein the sensor device removably attaches to an absorbent article. At 804, the sensor device can generate a replacement notification (e.g., via notification component 508) based on a determination that a triggering condition has been met. Triggering conditions include any of the triggering conditions described above, including the power level being at, near, or below a threshold power level; a performance level being at, near or below a threshold performance level, the power unit nearing or reaching the end of its expected life/runtime. At 806, the sensor device can (e.g., using notification component 508 and/or communication component 504) send the replacement notification to a device external to the sensor device (e.g., external user device 108), wherein based on the sending, the external device orders a replacement sensor device for an entity account associated with the sensor device (e.g., via ordering component 508).

Figure 9:
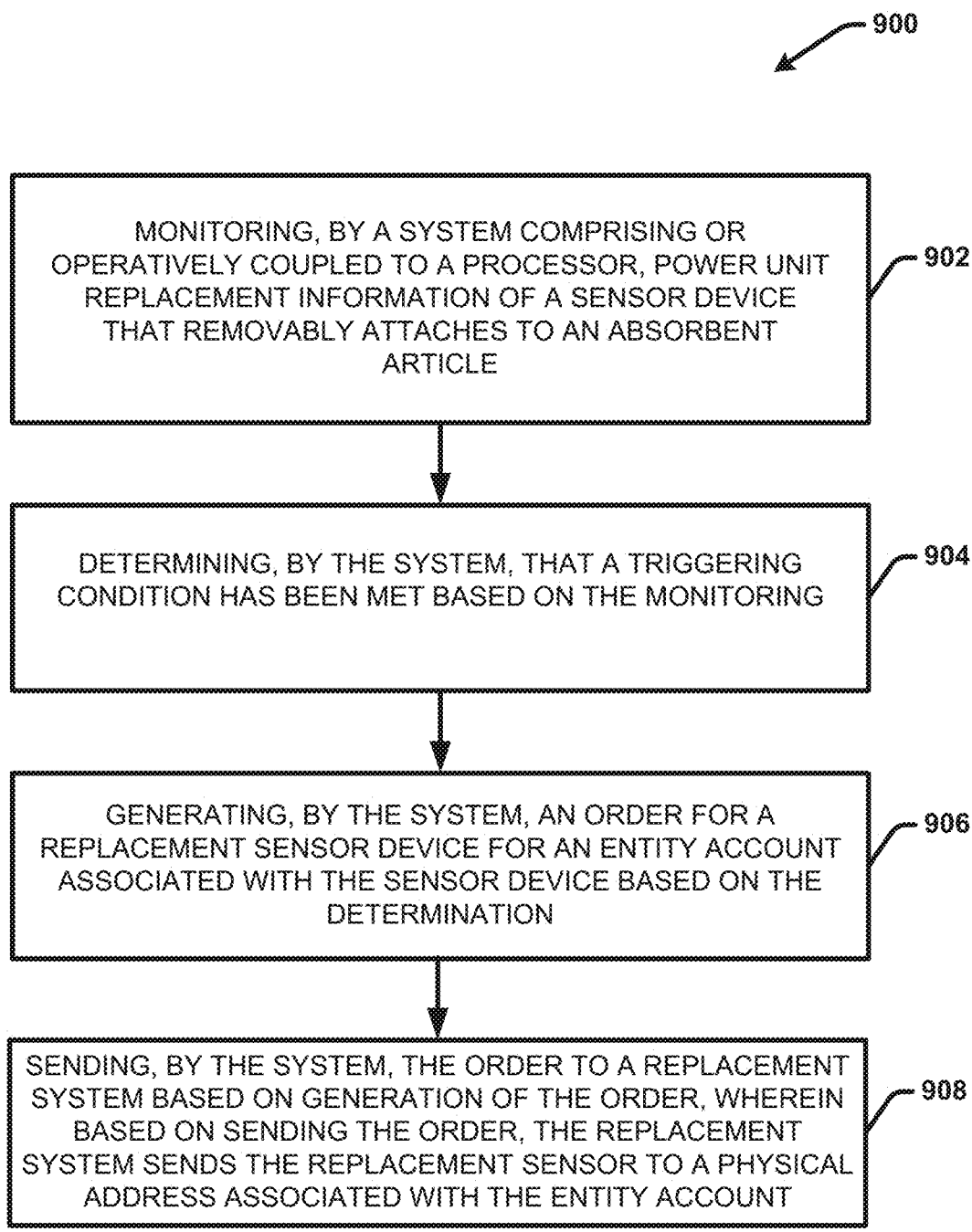
FIG. 9 presents a high-level flow diagram of another example process for replacing battery depleted sensor devices designed to be reused with absorbent articles in accordance with one or more embodiments of the disclosed subject matter.

FIG. 9 presents a high-level flow diagram of another example process 900 for replacing sensor devices, and/or power units for use in sensor devices, that are designed to be reused with absorbent articles. Repetitive description of like elements employed in respective embodiments is omitted for sake of brevity. At 902, a system comprising or operatively coupled to a processor can monitor power unit replacement information of a sensor device, wherein the sensor device removably attaches to an absorbent article. The system can monitor the power unit replacement information using the sensor device and/or an device external to the sensor device. At 904, the system determines a triggering condition has been met (e.g., via battery monitoring component 506 and/or battery monitoring component 604). Triggering conditions include any of the triggering conditions described above, including the power level being at, near, or below a threshold power level; a performance level being at, near or below a threshold performance level, the power unit nearing or reaching the end of its expected life/runtime. At 906, the system can generate an order for a replacement sensor device for an entity account associated with the sensor device based on the determination (e.g., via ordering component 608). At 908, the system can send the order to a replacement system based on generation of the order (e.g., via ordering component 608, and/or communication component 620), wherein the replacement system can send the replacement sensor to an address associated with the entity account (e.g., as provided in the user account database 722).

Figure 10:
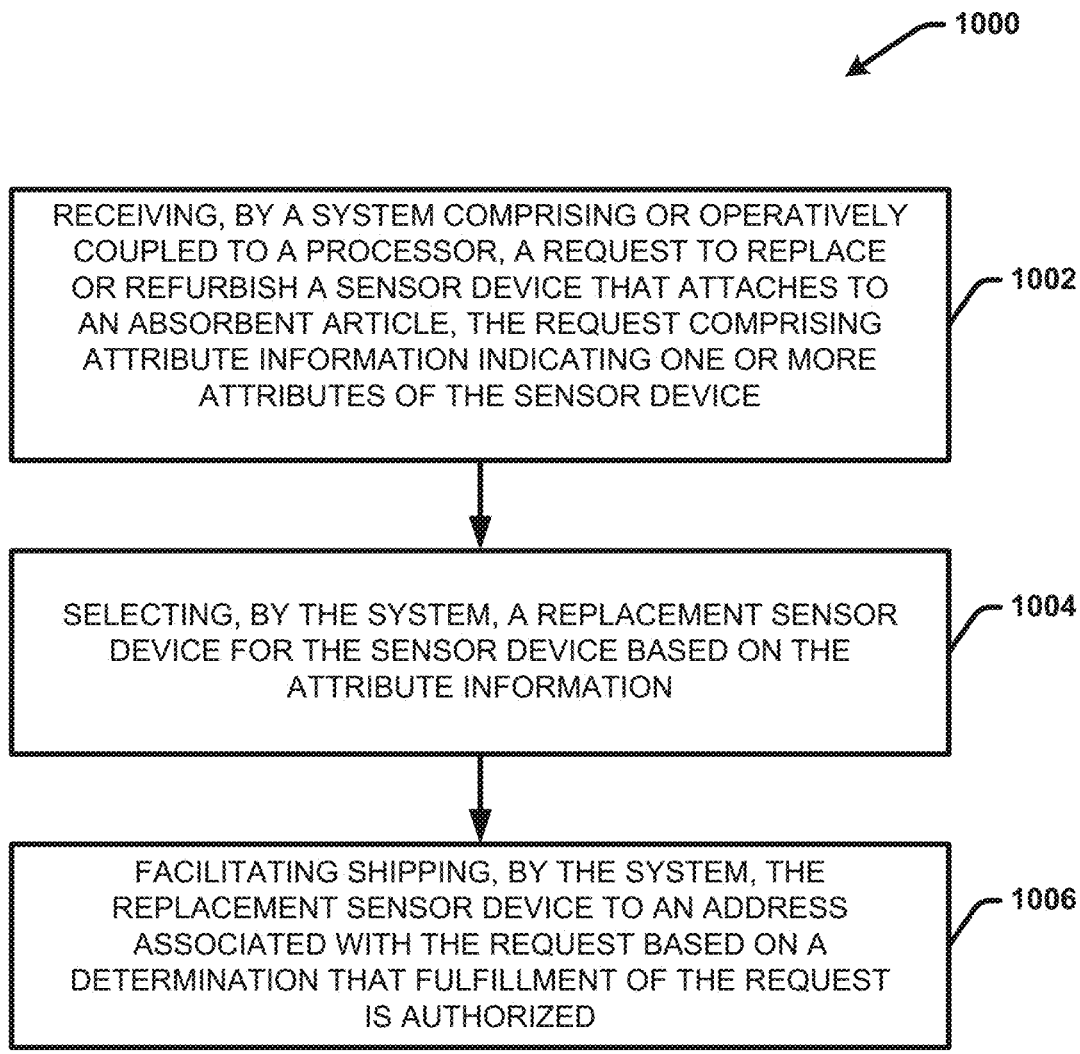
FIG. 10 presents a high-level flow diagram of another example process for replacing battery depleted sensor devices designed to be reused with absorbent articles in accordance with one or more embodiments of the disclosed subject matter.

FIG. 10 presents a high-level flow diagram of another example process 1000 for replacing sensor devices, and/or power units for use in sensor devices, that are designed to be reused with absorbent articles. Repetitive description of like elements employed in respective embodiments is omitted for sake of brevity. At 1002, a system (e.g., replacement system 116) comprising or operatively coupled to a processor can receive a request (e.g., via request receipt component 704) to replace or refurbish a sensor device that attaches to an absorbent article. The request can comprise attribute information indicating one or more attributes of the sensor device. For example, in various embodiments the attribute information can identify or indicate a serial number of the sensor device, a make of the sensor device, a model of the sensor device, a type of battery employed by the sensor device, a remaining lifespan of the battery, and the like. At 1004, the system can select a replacement sensor device for the sensor device based on the attribute information (e.g., via order processing component 706). At 1006, the system can further facilitate shipping the replacement sensor device to an address associated with the request based on a determination that fulfilment of the request is authorized (e.g., via the order processing component and using the shipping unit 124).

The present invention may be a system, a method, an apparatus and/or a computer program product at any possible technical detail level of integration. The computer program product can include a computer readable storage medium having computer readable program instructions thereon for causing a processor to carry out aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowcharts and block diagrams in the Figures illustrate the architecture, functionality, and operation of possible implementations of systems, methods, and computer program products according to various embodiments of the present invention. The functions noted in the blocks can occur out of the order noted in the Figures. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system comprising:
   a processor that executes computer executable components, the computer executable components comprising:
   a battery monitoring component that monitors a power level of a power unit of a sensor device that removably attaches to an absorbent article configured to absorb and contain bodily exudates; and
   a notification component that generates a replacement notification based on a determination that the power level is below a threshold power level,
   wherein the sensor device comprises an outer cover formed around the power unit, and wherein removal of the power unit from the outer cover renders the outer cover unusable with another power unit.

2. The system of claim 1, wherein the power unit comprises a non-rechargeable battery.

3. The system of claim 1, wherein the sensor device comprises the processor and wherein the notification component further sends the replacement notification to a device external to the sensor device.

4. The system of claim 1, wherein an external server device, a cloud-based system, an edge-based system and/or external user device comprises the processor.

5. The system of claim 4, wherein the computer executable components further comprise:
   an ordering component that generates an order for a replacement sensor device for an entity account associated with the sensor device based on the replacement notification.

6. The system of claim 5, wherein the ordering component further sends the order to a replacement system, and wherein the replacement system sends the replacement sensor device to an address associated with the entity account.

7. The system of claim 5, wherein the ordering component further presents a prompt at the device requesting authorization to place the order.

8. The system of claim 1, wherein the computer executable components further comprise:
   a reward component that associates a reward with an entity account associated with sensor device based on receipt of a replacement order, an input authorizing a replacement order, a purchase of a replacement, and/or a returned sensor device.

9. The system of claim 1, wherein the computer executable components further comprise:
   a return component that generates a return request with delivery instructions for returning the sensor device to a replacement system.

10. The system of claim 1, wherein the outer cover is formed via a proprietary mold.

11. A method comprising:
    monitoring, by a system comprising or operatively coupled to a processor, power unit replacement information of a sensor device, wherein the sensor device removably attaches to an absorbent article configured to absorb and contain bodily exudates, and wherein the sensor device comprises an outer cover formed around a power unit, and wherein removal of the power unit from the outer cover renders the outer cover unusable with another power unit; and
    generating, by the system, a replacement notification based on a determination that the sensor device is performing below a threshold performance level, a power level is below a threshold power level, a power unit has met a threshold time-in-use and/or age and combinations thereof.

12. The method of claim 11, wherein the system is embodied on or within the sensor device, and wherein the method further comprises:
    sending, by the system, the replacement notification to a device external to the sensor device for rendering at the device.

13. The method of claim 11, wherein the power unit replacement information is selected from the group consisting of: power level, age of power unit, age of sensor device, connectivity of power unit, runtime of sensor device, runtime of power unit, and combinations thereof.

14. The method of claim 11, further comprising:
generating, by the system, an order for a replacement sensor device for an entity account associated with the sensor device based on the replacement notification; and
sending, by the system, the order to a replacement system; and
sending, by the replacement system, the replacement sensor device to an address associated with the entity account.

15. The method of claim 11, further comprising:
rendering, by the system, the replacement notification at a device external to the sensor device in association with a prompt requesting authorization to place an order for a replacement sensor device; and
sending, by the system, the order for the replacement sensor device to a replacement system based on receipt of an input authorizing placement of the order.

16. The method of claim 11, further comprising:
issuing, by the system, a reward to an entity account associated with sensor device based on receipt of a replacement order, an input authorizing a replacement order, a purchase of a replacement, and/or a returned sensor device.

17. The method of claim 11, further comprising:
generating, by the system, a return request with delivery instructions for returning the sensor device to the replacement system.

\* \* \* \* \*